(12) United States Patent
Ouderkirk et al.

(10) Patent No.: US 11,559,201 B1
(45) Date of Patent: *Jan. 24, 2023

(54) SYSTEMS AND METHODS FOR EYE TRACKING USING MODULATED RADIATION

(71) Applicant: META PLATFORMS TECHNOLOGIES, LLC, Menlo Park, CA (US)

(72) Inventors: Andrew John Ouderkirk, Redmond, WA (US); Barry David Silverstein, Kirkland, WA (US); Brian Wheelwright, Sammamish, WA (US); Robin Sharma, Redmond, WA (US); Spencer Allan Wells, Seattle, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/233,035

(22) Filed: Apr. 16, 2021

Related U.S. Application Data

(63) Continuation of application No. 16/392,016, filed on Apr. 23, 2019, now Pat. No. 10,980,415.

(51) Int. Cl.
*A61B 3/113* (2006.01)
*G06F 3/01* (2006.01)
(Continued)

(52) U.S. Cl.
CPC .......... *A61B 3/113* (2013.01); *G02B 27/0093* (2013.01); *G06F 3/013* (2013.01);
(Continued)

(58) Field of Classification Search
CPC ................ A61B 3/113; G02B 27/0093; G02B 27/0172; G02B 2027/0138; G06F 3/013
(Continued)

(56) References Cited

U.S. PATENT DOCUMENTS 10,980,415 B1   4/2021  Ouderkirk et al.
2004/0170304 A1* 9/2004 Haven ................. G06V 20/597
                                                                   382/115
(Continued)

OTHER PUBLICATIONS

Golard et al., "Systems and Methods for Using Eye Tracking To Improve User Interactions With Objects In Artificial Reality", U.S. Appl. No. 16/354,835 dated Mar. 15, 2019, 80 pages.
(Continued)

*Primary Examiner* — Hai Tao Sun
(74) *Attorney, Agent, or Firm* — Greenberg Traurig, LLP

(57) ABSTRACT

Eye-tracking systems of the present disclosure may include at least one light source configured to emit modulated radiation toward an intended location for a user's eye. The modulated radiation may be modulated in a manner that enables the light source to be identified by detection and analysis of the modulated radiation. At least one optical sensor including at least one sensing element may be configured to detect at least a portion of the modulated radiation. A processor may be configured to identify, based on the modulated radiation detected by the optical sensor, the light source that emitted the modulated radiation. Various other methods, systems, and devices are also disclosed.

20 Claims, 13 Drawing Sheets

1000

1002
Emit, by at least one light source, modulated radiation toward a user's eye, the radiation being modulated in a manner that enables the light source to be identified 1004
Detect, by at least one optical sensor comprising at least one sensing element, at least a portion of the modulated radiation reflected off the user's eye 1006
Identify, by a processor and based on the modulated radiation reflected off the user's eye and detected by the optical sensor, the light source that emitted the modulated radiation

(51) Int. Cl.
  *G02B 27/00* (2006.01)
  *G02B 27/01* (2006.01)
(52) U.S. Cl.
  CPC .... *G02B 27/0172* (2013.01); *G02B 2027/014* (2013.01); *G02B 2027/0138* (2013.01)
(58) Field of Classification Search
  USPC .......................................................... 345/633
  See application file for complete search history.

(56) References Cited

U.S. PATENT DOCUMENTS

| | | | |
|---|---|---|---|
| 2012/0182265 A1 | 7/2012 | Smith et al. | |
| 2014/0268055 A1* | 9/2014 | Skogo | G06F 3/013 351/210 |
| 2016/0317056 A1 | 11/2016 | Moon et al. | |
| 2017/0235360 A1 | 8/2017 | George-Svahn | |
| 2017/0308159 A1* | 10/2017 | Yoon | G02B 27/0176 |
| 2017/0352178 A1* | 12/2017 | Katz | G02B 27/0093 |
| 2018/0031865 A1* | 2/2018 | Hyde | A61F 2/1656 |

OTHER PUBLICATIONS

Pre-Interview First Office Action received for U.S. Appl. No. 16/392,016 dated Apr. 28, 2020, 17 pages.

Final Office Action received for U.S. Appl. No. 16/392,016 dated Jul. 23, 2020, 30 pages.

Non-Final Office Action received for U.S. Appl. No. 16/392,016 dated Nov. 2, 2020, 34 pages.

Non-Final Office Action received for U.S. Appl. No. 16/392,016 dated Nov. 23, 2020, 38 pages.

Notice of Allowance received for U.S. Appl. No. 16/392,016 dated Feb. 24, 2021, 34 pages.

* cited by examiner

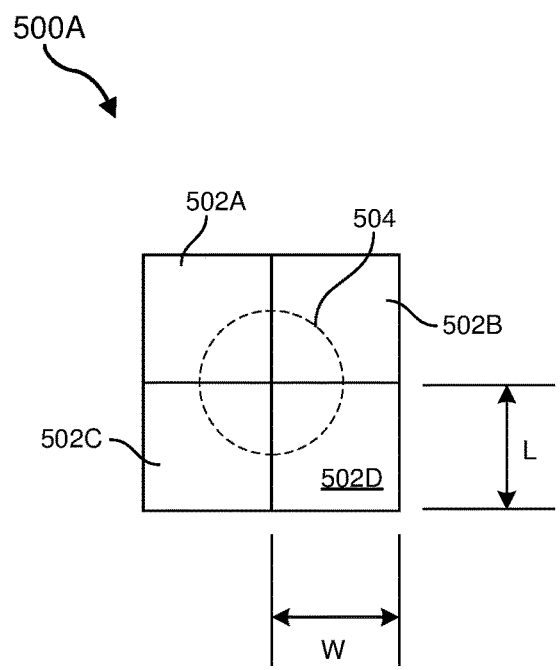
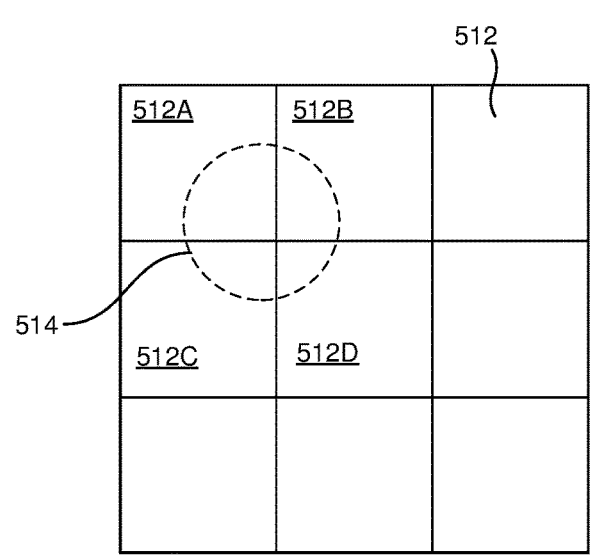
FIG. 5A  FIG. 5B

SYSTEMS AND METHODS FOR EYE TRACKING USING MODULATED RADIATION

CROSS REFERENCE TO RELATED APPLICATION

This application is a continuation of U.S. patent application Ser. No. 16/392,016, filed 23 Apr. 2019, the entire disclosure of which is incorporated herein by reference.

BRIEF DESCRIPTION OF THE DRAWINGS

The accompanying drawings illustrate a number of example embodiments and are a part of the specification. Together with the following description, these drawings demonstrate and explain various principles of the instant disclosure.

FIGS. 5A and 5B are plan views of respective optical sensors including sensing elements, according to at least some embodiment of the present disclosure.

Figure 1:
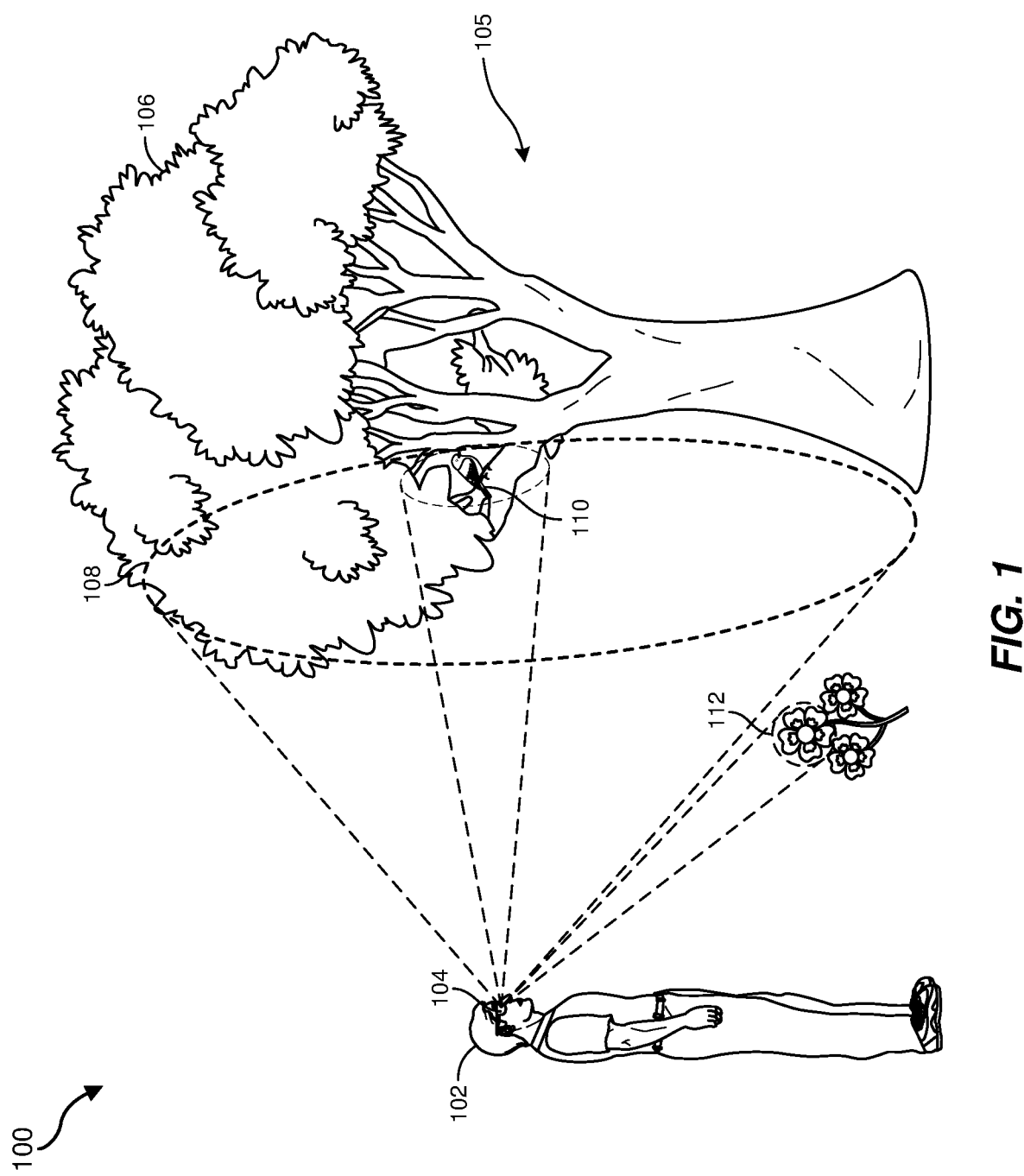
FIG. 1 is an illustration of an example environmental context in which an eye-tracking system may be used, according to at least one embodiment of the present disclosure.

Throughout the drawings, identical reference characters and descriptions indicate similar, but not necessarily identical, elements. While the example embodiments described herein are susceptible to various modifications and alternative forms, specific embodiments have been shown by way of example in the drawings and will be described in detail herein. However, the example embodiments described herein are not intended to be limited to the particular forms disclosed. Rather, the instant disclosure covers all modifications, equivalents, and alternatives falling within the scope of the appended claims.

DETAILED DESCRIPTION OF EXAMPLE EMBODIMENTS

Artificial-reality systems (e.g., virtual-reality systems, augmented-reality systems, mixed-reality systems, and hybrid-reality systems) typically include a display element configured to present images of real and/or virtual scenes and objects to users. Some artificial-reality systems also include an eye-tracking subsystem designed to track a user's eye to determine where the user is looking. Unfortunately, conventional eye-tracking subsystems often generate an excessive amount of data per time unit, typically due to their reliance on relatively high frame rate and/or high-resolution sensors. This may, in turn, result in increased computational latency and bottlenecks, which may degrade the overall user experience.

For example, conventional eye-tracking systems often use relatively high-resolution cameras to track a user's eye. These cameras typically include arrays of optical sensing elements with relatively high pixel counts (e.g., kilopixel or megapixel arrays), which may require relatively high bandwidth backend processing. For example, such conventional eye-tracking systems may generate and process megabits of data per second due to their reliance on relatively high frame rate and/or high-resolution sensors. Generating and/or processing megabits of data per second may require significant computational capabilities (e.g., fast processors, an increased memory footprint, high power, etc.) and/or an increased physical footprint to house larger sensor arrays and associated backend electronics. In addition, eye-tracking systems that employ detection of reflected light may be susceptible to noise resulting from ambient light (e.g., light from a real-world environment, light from an electronic display, light from thermal radiation, etc.).

The present disclosure is generally directed to systems and methods for eye tracking using addressable (e.g., identifiable and individually drivable) light sources and optical sensors. The light sources may be configured to emit modulated radiation and the optical sensors may be positioned and configured to detect the modulated radiation, such that the radiation reflected off the eye and originating from the individual light sources may be identified and mapped. The modulated radiation may also facilitate the filtering out of noise in connection with data from the optical sensors.

Figure 2:
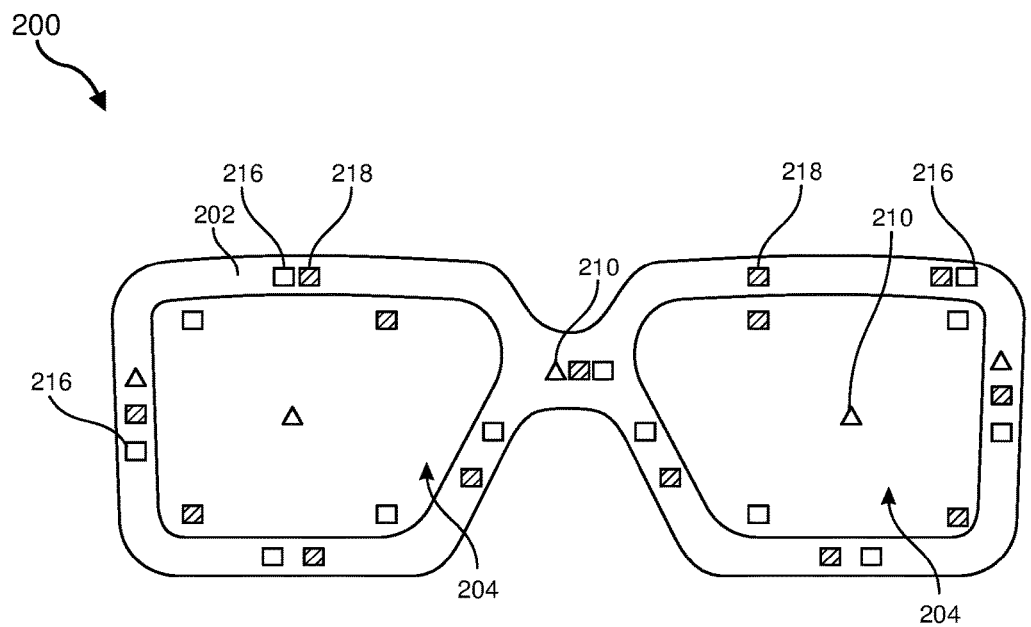
FIG. 2 is a schematic back (i.e., user's) view of an example head-mounted display ("HMD") including an eye-tracking system according to at least one embodiment of the present disclosure.
Figure 3:
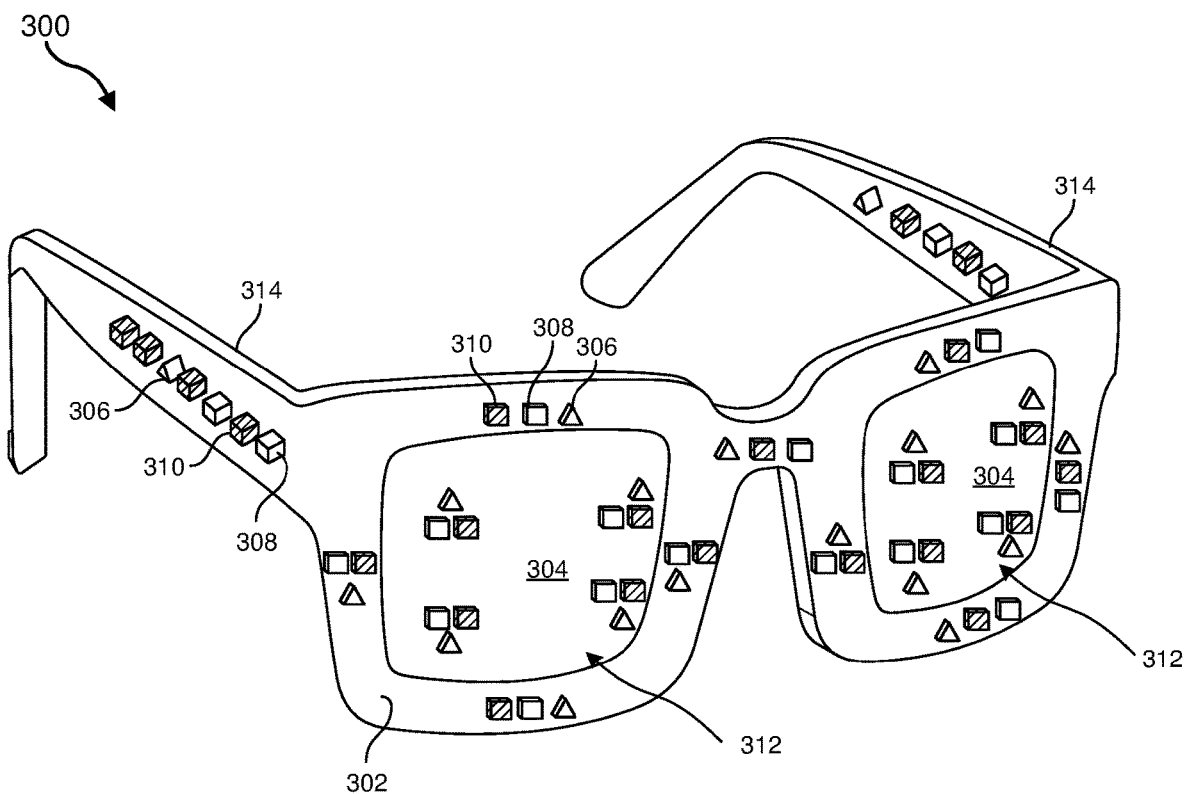
FIG. 3 is a schematic perspective view of an example head-mounted display ("HMD") including an eye-tracking system according to at least one embodiment of the present disclosure.
Figure 4:
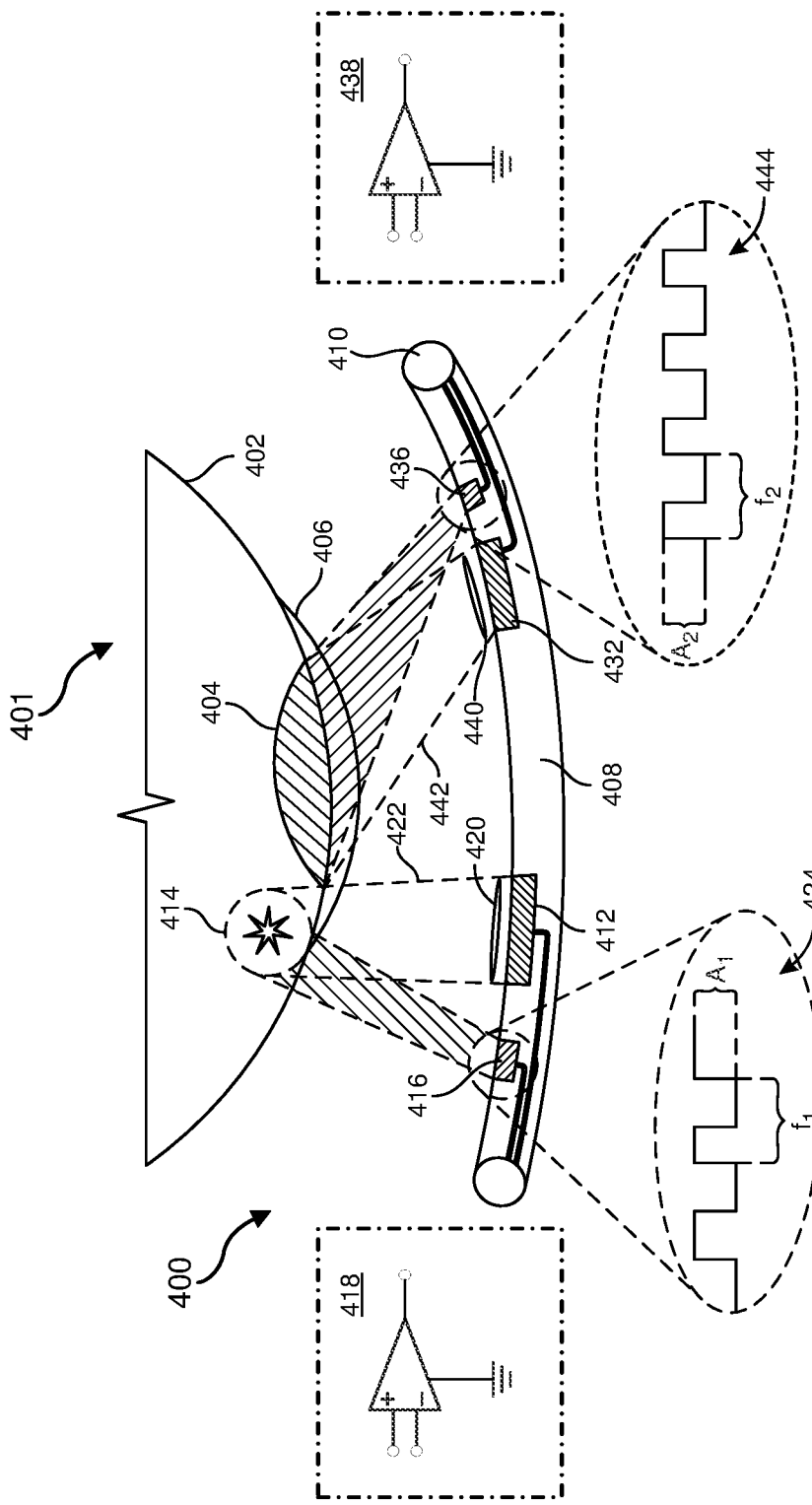
FIG. 4 is a top view of an eye-tracking system positioned with respect to a user's eye, according to at least one embodiment of the present disclosure.
Figure 6:
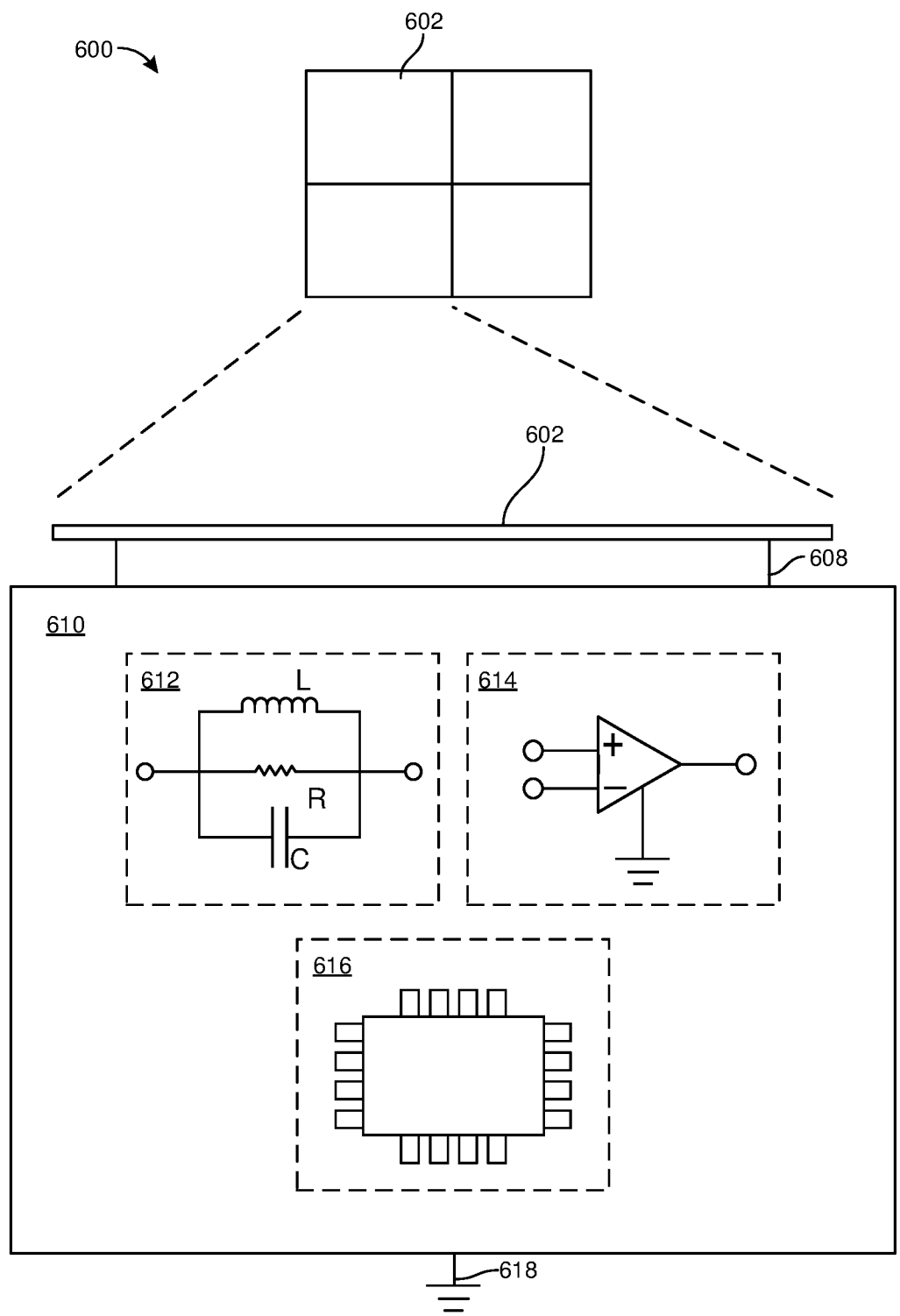
FIG. 6 shows an example optical sensor and associated backend electronics, according to at least one embodiment of the present disclosure.
Figure 7:
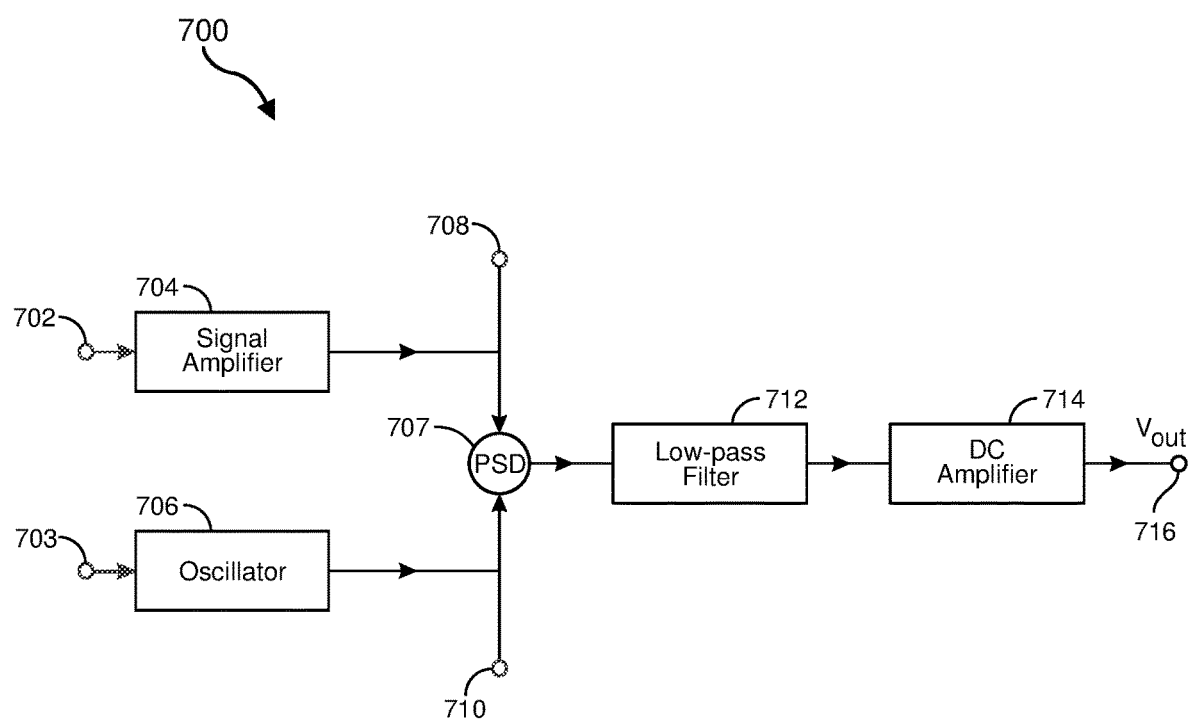
FIG. 7 is a schematic diagram for an amplifier system that may be used in connection with eye-tracking systems, according to at least one embodiment of the present disclosure.
Figure 8A:
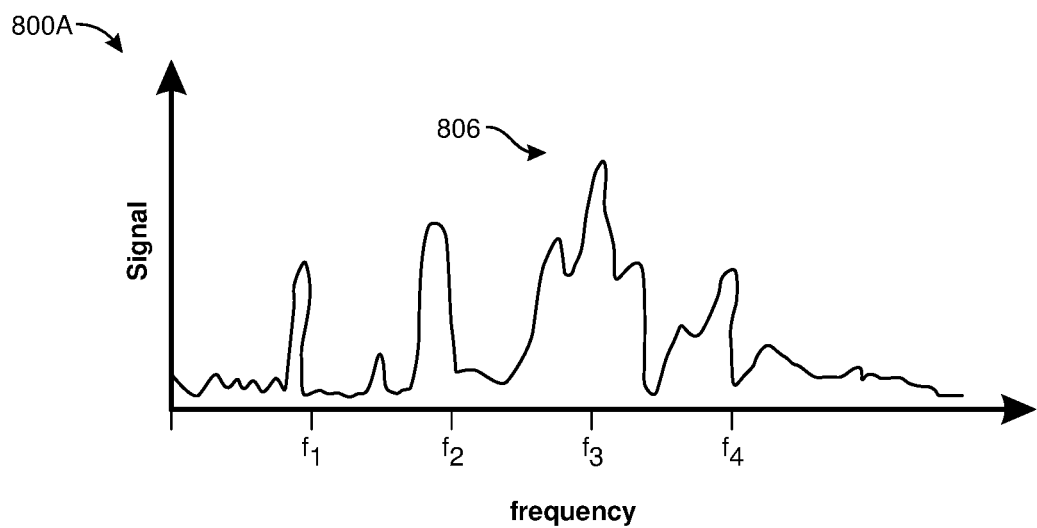
FIG. 8A shows a plot of an unprocessed signal of an optical sensor without the use of an amplifier system, such as the amplifier system of FIG. 7, according to at least one embodiment of the present disclosure.
Figure 8B:
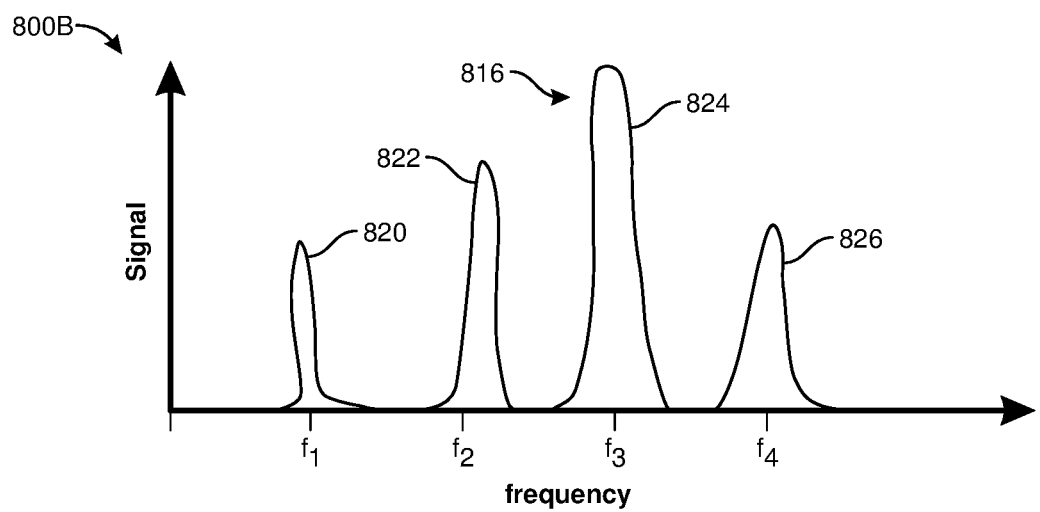
FIG. 8B shows a plot of a signal of an optical sensor with the use of an amplifier system, such as the amplifier system of FIG. 7, according to at least one embodiment of the present disclosure.
Figure 9A:
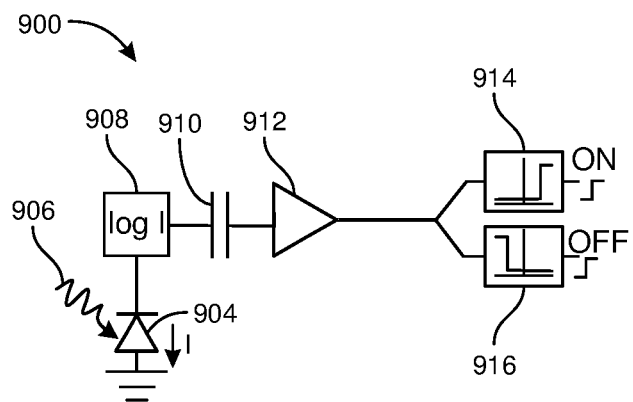
FIG. 9A is a schematic illustration of an optical sensing system, according to at least one embodiment of the present disclosure.
Figure 9B:
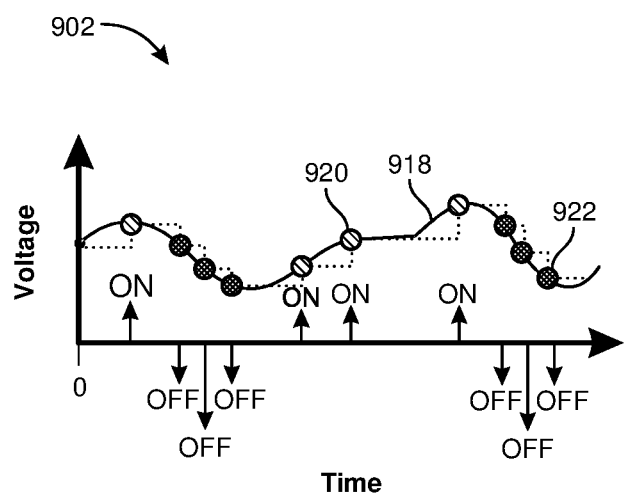
FIG. 9B is a plot showing an example voltage output of the optical sensing system of FIG. 6A over time, according to at least one embodiment of the present disclosure.
Figure 10:
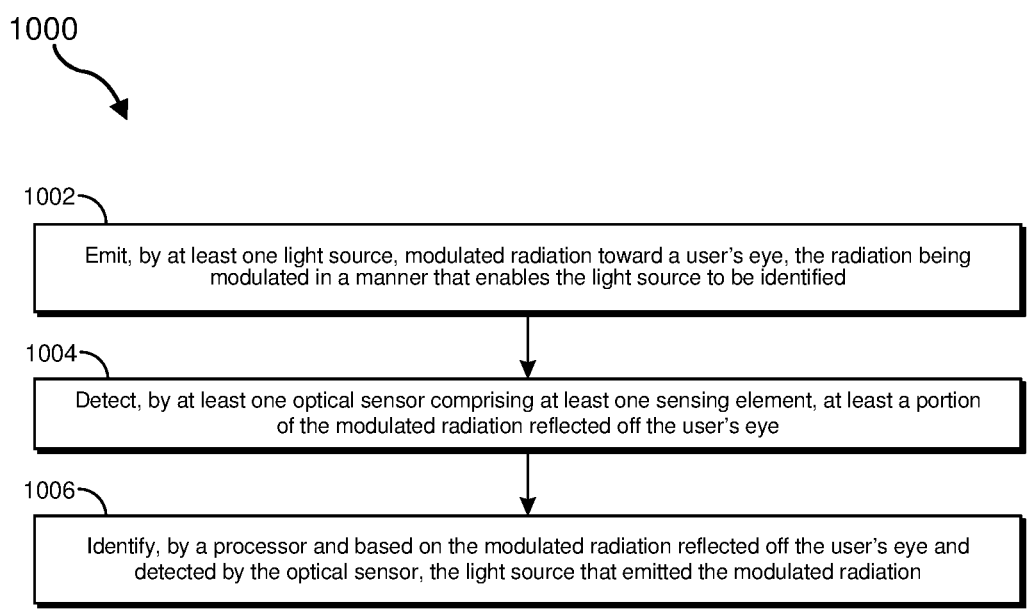
FIG. 10 is flow diagram of a method for eye tracking, according to at least one embodiment of the present disclosure.
Figure 11:
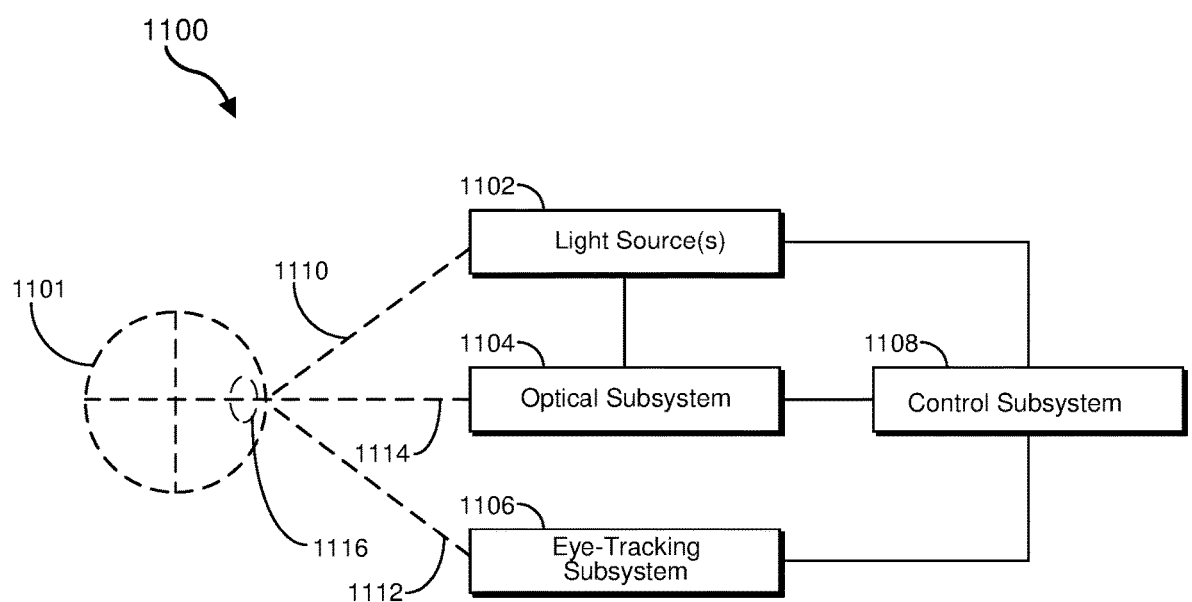
FIG. 11 is schematic illustration of a display system, according to at least one embodiment of the present disclosure.

The following will provide, with reference to FIG. 1, detailed descriptions of an example environmental context in which eye-tracking systems of the present disclosure may be used. With reference to FIGS. 2-4, the following will provide detailed descriptions of example eye-tracking systems. With reference to FIGS. 5A and 5B, the following will provide detailed descriptions of example optical sensors. With reference to FIG. 6, detailed descriptions of example optical sensors and associated backend electronics will be provided. With reference to FIG. 7, the following will provide detailed descriptions of example amplifier systems. With reference to FIGS. 8A and 8B, the following will provide detailed descriptions of signal outputs of optical sensors without and with processing through amplifier systems. With reference to FIGS. 9A and 9B, the following will provide detailed descriptions of an example optical sensing system and its voltage output over time, respectively. With reference to FIG. 10, the following will provide detailed descriptions of an example method for eye tracking. With reference to FIG. 11, detailed descriptions of an example display system will be provided. With reference to FIGS. 8-10, the following will provide detailed descriptions of various example artificial-reality systems that may be used in connection with embodiments of this disclosure.

FIG. 1 shows an example environmental context 100 in which eye-tracking systems of the present disclosure may be used. A user 102 may view a scene through or in an HMD 104, which may include an eye-tracking system. The eye-tracking system of the HMD 104 may include a plurality of optical sensors (e.g., optical sensor arrays or optical sensors including a single photosensitive sensing element) positioned thereon, such as including at least one low-resolution optical sensor, for sensing a position of the user's 102 eye or eyes, as described in further detail below. Each of the optical sensors in the plurality of optical sensors may be positioned and configured to detect a respective portion of radiation reflected from the eye of the user 102. The radiation may be directed toward the eye of the user 102 via one or more light sources, which may emit modulated radiation to enable the eye-tracking system to identify (e.g., uniquely identify) the particular light source from which the radiation originates.

In some examples, a "low-resolution" optical sensor may refer to an optical sensor array that employs a low number of (e.g., about one hundred or fewer, about thirty-six or fewer, about nine or fewer, about four or fewer, etc.) sensing elements. In some embodiments, each of the sensing elements of a low-resolution optical sensor may have a lateral length of at least about 5 μm and a lateral width of at least about 5 μm. In contrast, in some examples, a "high-resolution" optical sensor may refer to an optical sensor array that employs a relatively higher number of sensing elements than a low-resolution optical sensor array, such as a kilo-pixel or megapixel (or multiple kilo-pixels or multiple megapixels) optical sensor array. A high-resolution optical sensor may also employ sensing elements that are have a lateral length of less than about 5 μm and a lateral width of less than about 5 μm.

The HMD 104 may be or include an artificial-reality system, such as a virtual-reality system or an augmented-reality system. For example, the user 102 may view a scene through an optical element (e.g., a lens, a combiner lens, a waveguide, a hot mirror, etc.) of the HMD 104. The scene may include real-world and/or virtual objects 105 (e.g., a real or virtual tree 106, a real or virtual bird 108, a real or virtual flower 110, etc.). The objects 105 may be at different locations in the user's 102 field of view and/or at different distances or perceived distances relative to the user 102.

The eye-tracking system of the HMD 104 may be used to analyze and determine the eye position, movement, and/or gaze of the user 102, such as when the user 102 shifts between different views of the objects 105 (e.g., the tree 106, the bird 108, and the flower 110) viewed through or in the HMD 104. Data relating to the user's 102 eye position and/or gaze may be used to perform a variety of tasks, such as to ascertain which object 105 is being viewed by the user 102 at a given time, to adjust an optical property (e.g., focal length) of the HMD 104, to adjust a blur or defocus of a virtual image displayed on the HMD 104, to alter a shape of a virtual image displayed on the HMD 104, to shift a position of a virtual image displayed by the HMD 104, to enable the user 102 to make a selection of a viewed object 105, to provide different virtual content (e.g., visual, auditory, haptic, etc.) and information to the user 102 depending on where the user 102 looks, to calibrate the HMD 104 and/or the eye-tracking system thereof, etc.

In the case of calibration, a supervised technique may involve the user 102 being directed to gaze at one or more of the objects 105 at a known time and/or in a known pattern, and the eye-tracking system of the HMD 104 may record values that correspond to the user's eye position and gaze data. Unsupervised techniques may involve predicting or analyzing where the user 102 is looking without being directed to look in a particular direction or at a particular object 105. In some examples, a combination of supervised, unsupervised, semi-supervised, and/or reinforced learning techniques may be used for calibrating the eye-tracking system of the HMD 104. In some embodiments, the calibration may employ a low-resolution optical sensor array and/or a higher-resolution optical sensor array to determine the eye position and gaze of the user 102.

In some examples, the disclosed systems may use eye tracking to first identify the user's 102 field of view 112 and/or the eye gaze of the user 102 (i.e., the location within a scene on which the eyes of the user 102 are focused). The disclosed systems may then identify (using, e.g., machine-learning or computer-vision algorithms) an object 105 in the field of view 112 and/or an object 105 on which the user's 102 gaze is focused (such as the tree 106, the bird 108, or the flower 110).

The disclosed systems may track the eye(s) of the user 102 (and thus determine the eye gaze and/or field of view 112 of the user 102) using any of a variety of eye-tracking systems and techniques. In one example, the disclosed systems may track the eye(s) by tracking the movement of the user's 102 pupil and/or using so-called glints (also known as corneal reflections or Purkinje images) reflected off the eye. Additional discussions regarding eye-tracking systems and techniques are provided below, such as in connection with FIGS. 2-7.

The systems described herein may identify the objects 105 in a user's 102 field of view 112 and/or an object 105 on which the user's 102 gaze is focused in a variety of ways. In one embodiment, the disclosed systems may first analyze a scene (such as the environmental context 100 in FIG. 1) using an object-recognition algorithm (e.g., using a machine-vision algorithm), which may allow for the scene to be mapped into a number of objects that may be analyzed computationally by a processor of a device. This scene may be pre-mapped or may be mapped in real time or near real time. In one example, the scene may include information derived from an indoor map or from an outdoor map and/or may include information based on global-positioning system (GPS) signals or similar locational signals.

The eye-tracking system of the HMD 104 may exhibit characteristics to ensure that an optical sensor thereof meets a predetermined information output constraint, such as bandwidth, output speed, power level, accuracy, a combination thereof, or the like. For example, one or more of the optical sensors for eye tracking may exhibit a low resolution compared to conventional optical sensors used for eye tracking. Thus, the optical sensors according to the present disclosure may produce data at a rate below a predetermined threshold, which may result in efficient (e.g., energy efficient, bandwidth efficient, etc.) eye tracking. Non-limiting examples of such characteristics of a given optical sensor may include a sensing element size, a number of sensing elements, an overall spatial resolution of the optical sensor, an angular position of the sensor with respect to a user's eye, a frequency range of detection for the sensing elements, response times of the sensing elements, combinations thereof, and/or the like.

The HMD 104 may include a processor and/or a memory configured to perform eye tracking locally on the HMD 104. Alternatively or additionally, the processor and/or memory may be coupled to a transceiver, which may be part of the HMD 104. The transceiver may be used to perform eye tracking at least partially on an external device. The external device may include a third-party server, a cloud-based server, a user device such as a mobile device, a tablet, a computer, combinations thereof, and/or the like.

FIG. 2 is a schematic back (i.e., user's) view of an example HMD 200 including an eye-tracking system. The HMD 200 may include a frame 202 that supports one or more optical elements 204 (e.g., an optical lens, a combiner lens, a waveguide, a hot mirror, etc.) on or through which a user may view a real-world and/or virtual image. Depending on the type of HMD 200, one or more electronic displays may be associated with the optical elements 204, such as for displaying virtual content or a reproduction of real-world content to the user. Non-limiting examples of the electronic display include a liquid crystal display ("LCD"), a light emitting diode ("LED") display, a microLED display, an organic light emitting diode ("OLED") display, an active-matrix OLED display ("AMOLED"), a transparent OLED display ("TOLED"), a laser-based display, a liquid crystal on silicon ("LCoS") display, a scanning source (e.g., a scanning laser), a waveguide, an image combiner lens, combinations thereof, and/or the like.

The eye-tracking system of the HMD 200 may include one or more light sources 210 (represented in FIG. 2 by triangles) for directing radiation (e.g., infrared or visible radiation) toward the eye(s) of the user and one or more first optical sensors 216 (represented in FIG. 2 by empty squares) for sensing radiation (e.g., infrared or visible radiation) reflected from the user's eye(s). In some embodiments, the eye-tracking system may optionally include one or more second optical sensors 218 (represented in FIG. 2 by hatched squares) that may exhibit a higher resolution than the first optical sensors 216 (e.g., by having an increased quantity of sensing elements and/or smaller sensing elements). The second optical sensors 218, if present, may be used for eye tracking less frequently than the first sensors 216, such as for calibration operations and/or periodically to confirm or adjust an analysis of data from the first sensors 216.

The light sources 210, the first optical sensors 216, and the second optical sensors 218 (if present) may be positioned in a variety of locations on the HMD 200. As shown in FIG. 2, these components may be positioned on or embedded within different locations along the frame 202 and/or on or embedded within the optical element 204 and within an optical aperture of the optical element 204. In some examples, the "optical aperture" of an optical element may refer to a portion of the optical element through which a user is intended to view a real-world or virtual image. If positioned within the optical aperture of the optical element 204, the light sources 210, first optical sensors 216, and second optical sensors 218 (and any conductive material for providing electrical access thereto, e.g., conductive traces) may be formed of a material and/or at a size that is substantially invisible or transparent to visible light when the HMD 200 is in use. For example, the light sources 210, first optical sensors 216, and second optical sensors 218 positioned within the optical aperture may be about 200 μm (in length and/or width) or less, such as about 100 μm or less. Similarly, conductive traces for providing electrical access to these components may have a line width of about 200 μm or less, such as about 100 μm or less.

In some embodiments, multiple light sources 210 may be distributed at different locations on the HMD 200, such as along the frame 202, on or embedded within the optical elements 204, and/or along a temple portion of the frame 202. The light sources 210 may direct radiation (e.g., infrared or visible radiation) directly toward the user's eye or indirectly toward the user's eye, such as by reflecting off or redirecting through the optical elements 204 (e.g., a hot mirror, an image combiner lens, a waveguide, etc.). For example, the light sources 210 may be or include an infrared light-emitting diode ("IRED"). Having multiple light sources 210 may ensure that radiation reaches the user's eye in many different conditions and states, such as when the user's eyelid or eyelashes block radiation from one or more of the light sources 210, when the user looks in different directions, when the user's eye or eyelid anatomy varies, etc.

In some examples, one or more of the light sources 210 may emit modulated radiation, such as radiation having different wavelengths, waveforms, pulsed or durational timing, etc., to enable the eye-tracking system to determine the origin of detected radiation reflected from the user's eye. Such modulated radiation may enable the particular light source 210 of radiation detected by the first or second optical sensors 216, 218 to be determined with increased certainty for improved eye tracking and/or for reducing the effects of ambient radiation (e.g., noise).

Likewise, multiple first optical sensors 216 may be distributed at different locations on the HMD 200, such as along the frame 202 and/or on or embedded within the optical elements 204. The first optical sensors 216 may be located at positions such that at least one of the first optical sensors 216 may have a view of the user's eye at all or substantially all times when the user's eye is open and when the HMD 200 is in use. Examples of suitable optical sensors for the first optical sensors 216 and associated systems and components are described below with reference to FIGS. 4-7, 9A, and 11.

The presence of the first optical sensors 216 may improve an efficiency and/or speed of the eye-tracking system of the HMD 200 compared to conventional eye-tracking systems. For example, the relatively low resolution of the first optical sensors 216 may require less power, a smaller physical footprint, less processing resources, and/or less bandwidth than comparably higher resolution optical sensors (e.g., HD cameras, etc.), while still outputting data sufficient to effectively determine a position of the user's eye. In some cases, certain characteristics of the low-resolution first optical sensors 216 may be superior to relatively higher resolution optical sensors, such as frame rate, light sensitivity, signal-to-noise ratio ("SNR"), etc.

FIG. 3 is a schematic perspective view of an example HMD 300 including an eye-tracking system. The HMD 300 may be similar to the HMD 200 described above with reference to FIG. 2. For example, as shown in FIG. 3, the HMD 300 may include a frame 302 that supports one or more optical elements 304, which may include and/or define an optical aperture 312. One or more electronic displays may be associated with the optical elements 304, such as for displaying virtual content or a reproduction of real-world content to the user. The eye-tracking system of the HMD 300 may include one or more light sources 306 (represented in FIG. 3 by triangles) for directing modulated radiation toward the eye(s) of the user and one or more first optical sensors 308 (represented in FIG. 3 by empty squares or cubes) for sensing radiation reflected from the user's eye(s). The first optical sensors 308 may be low-resolution optical sensors 308. The eye-tracking system may include one or more second optical sensors 310 (represented in FIG. 3 by hatched squares) that may exhibit a higher resolution than the first optical sensors 308. The frame 302 may include temple portions 314.

FIG. 3 generally illustrates additional locations on the HMD 300 where the light sources 306, the first optical sensors 308, and the second optical sensors 310 may be positioned.

For ease of illustration, some of the light sources 306, first optical sensors 308, and second optical sensors 310 may appear to be located on outer (e.g., away from a user) surfaces of the HMD 300 in FIG. 3. However, it is to be understood that the light sources 306, first optical sensors 308, and second optical sensors 310 may typically be located on inner (e.g., facing the user) surfaces of the HMD 300, such that radiation can be directed from the light sources 306 to the user's eye(s) either directly or indirectly (e.g., via a reflective surface, a hot mirror, an image combiner, a waveguide, etc.), and the radiation reflected from the user's eye(s) can be detected by the optical sensors 308, 310 either directly or indirectly.

FIG. 4 is a top view of an eye-tracking system 400 positioned with respect to a user's eye 401. The user's eye 401 includes a sclera 402, a pupil 404, and a cornea 406. The eye-tracking system 400 may include an optical element 408, which may be supported by a frame 410.

The eye-tracking system 400 may include a plurality of optical sensors 412, 432. The optical sensors 412, 432 may be low-resolution optical sensor arrays (e.g., including about one hundred or fewer sensing elements), high-resolution optical sensor arrays (e.g., including more than one hundred sensing elements, such as a kilopixel(s) or megapixel(s) optical sensor array), an optical sensor with a single photo-sensitive sensing element, or a combination thereof. A first optical sensor 412, which may be configured for detecting radiation in the form of a glint 414 reflected off the user's eye 401 for eye-tracking purposes, may be positioned on or embedded within the optical element 408 and/or the frame 410. The first optical sensor 412 may be an optical sensor array that includes a plurality of photoactive sensing elements or an optical sensor that includes a single photoactive sensing element (e.g., a position-sensing detector, as described below).

A first light source 416 may be positioned and configured to project the glint 414 toward the user's eye 401. The first light source 416 may emit modulated radiation 424 so the first optical sensor 412 may identify (e.g., uniquely identify) the first light source 416 as the source of the glint 414. For example, the modulated radiation 424 associated with the glint 414 may have a unique waveform, such as pulsed with a first amplitude $A_1$ and at a first frequency $f_1$. The first amplitude $A_1$ and the first frequency $f_1$ may be different (e.g., unique) compared to other radiation (e.g., other glints from other light sources, radiation from the environment, radiation from an electronic display, etc.) directed toward the user's eye 401.

When the first optical sensor 412 detects the modulated radiation 424 (e.g., exhibiting the first amplitude $A_1$ and the first frequency $f_1$), the eye-tracking system 400 may be able to identify the first light source 416 as the source of the glint 414 associated with the detected modulated radiation 424 with increased (e.g., substantially complete) certainty.

A first amplifier 418 may be associated with the first optical sensor 412, such as to amplify and/or to identify characteristics of detected signals. For example, the first amplifier 418 may include a lock-in amplifier and/or a low-noise amplifier ("LNA"). An example lock-in amplifier is described below with reference to FIG. 7. The lock-in amplifier, if employed by the first amplifier 418, may determine a frequency and/or phase of the modulated radiation 424 emitted by the first light source 416. In some examples, the lock-in amplifier may be referenced to the first frequency $f_1$ of the modulated radiation 424.

If an LNA is employed by the first amplifier 418, the LNA may include various parameters that may be selected or determined to amplify signals from the first optical sensor 412. For example, the LNA may be configured to exhibit a noise figure below a predetermined threshold.

In some examples, one or more micro-lenses 420 may be positioned on or over sensing elements of the first optical sensor 412 for focusing or defocusing radiation reflected from the user's eye 401 relative to the sensing elements. The first optical sensor 412 may have a field of view ("FOV") 422 through the associated micro-lens(es) 420. The FOV 422 may represent a cone or other area within which light reflected from the user's eye 401 may reach the first optical sensor 412.

A position of the glint 414 on the user's eye 401 may be ascertained by detecting the amount of radiation (e.g., infrared radiation) detected by the sensing element(s) of the first optical sensor 412, or detected by the first optical sensor 412 and/or other similar optical sensors. For example, in an embodiment in which the first optical sensor 412 includes an array of multiple sensing elements, if radiation (or more radiation) is detected in a first one of the sensing elements compared to a second one of the sensing elements, it may be determined that the glint 414 (or a larger portion thereof) is positioned on a portion of the FOV 422 associated with the first one of the sensing elements. Similarly, if radiation (or more radiation) is detected by the first optical sensor 412 compared to another optical sensor, it may be determined that the glint 414 (or a larger portion thereof) is positioned within the FOV 422 associated with the first optical sensor 412 rather than an FOV associated with the other optical sensor.

As the user's eye 401 moves (e.g., to look in a different direction), at least a portion of the glint 414 may reflect from different surfaces on the user's eye 401, such as from the sclera 402 to the cornea 406. Because the curvature and surface angle of the cornea 406 is different from the curvature and surface angle of the sclera 402, the radiation of the glint 414 may be detected (or detected more or less) by different portions (e.g., different sensing elements) of the first optical sensor 412 or by different optical sensors. Such changes may be analyzed by the eye-tracking system 400 to determine a position of the user's eye 401 relative to the optical element 408.

Similar concepts may be also applicable to pupil tracking, as opposed to or in addition to glint tracking. For example, a second optical sensor 432, which may be configured for detecting a position of the pupil 404 of the user's eye 401 for eye-tracking purposes, may be positioned on or embedded within the optical element 408 and/or the frame 410. The second optical sensor 432 may include a single photoactive sensing element or an array of photoactive sensing elements.

A second light source 436 may be positioned and configured to project radiation (e.g., infrared radiation) toward the user's eye 401, to facilitate tracking of the pupil 404. For example, the radiation may readily reflect off the sclera 402 and the iris (not shown) of the user's eye 401, but may not reflect (or may reflect less) from the pupil 404. In this case, the second optical sensor 432 may be configured to detect radiation reflected off the sclera 402 and iris, and/or a lack of radiation at the location of the pupil 404. Alternatively, if the second optical sensor 432 and the second light source 436 are positioned and configured in front of the user's line of sight, the radiation emitted from the second light source 436 may readily reflect off the user's retina through the pupil 404, but may reflect less from the sclera 402 and iris, similar the red-eye effect observed in flash photography. In this case, the second optical sensor 432 may be configured to detect radiation reflected off the retina through the pupil 404.

The second light source 436 may emit modulated radiation 444 so the second optical sensor 432 may identify (e.g., uniquely identify) the second light source 436 as the source of light detected in connection with tracking the pupil 404. For example, the modulated radiation 444 associated with the second light source 436 may be pulsed, with a second amplitude $A_2$ and at a second frequency $f_2$, which may be different (e.g., unique) compared to other radiation (e.g., glints, radiation from other light sources, radiation from the environment, radiation from an electronic display, radiation from the first light source 416, etc.) directed toward the user's eye 401. Thus, when the second optical sensor 432 detects the modulated radiation 444 (e.g., exhibiting the second amplitude $A_2$ and the second frequency $f_2$), the eye-tracking system 400 may be able to identify the second light source 436 as the source of light associated with tracking the pupil 404 with increased (e.g., substantially complete) certainty.

A second amplifier 438 may be associated with the second optical sensor 432, such as to amplify and/or to identify characteristics of detected signals, as described above with reference to the first amplifier 418.

In some examples, one or more micro-lenses 440 may be positioned on or over the second optical sensor 432 for focusing or defocusing radiation reflected from the user's eye 401 relative to the sensing elements thereof. The second optical sensor 432 may have a respective FOV 442 through the associated micro-lens(es) 420. The FOV 442 may represent a cone or other area within which light reflected from the user's eye 401 may reach the second optical sensor 432. The diameter of the microlens 420 and associated sensor, and any associated packaging, may be less than about 200 μm, such as less than about 100 μm.

A position of the pupil 404 of the user's eye 401 may be ascertained by detecting the amount of radiation (e.g., infrared radiation) detected by the various sensing elements of the second optical sensor 432, similar to the procedure described above with reference to the first optical sensor 412. However, rather than correlating a presence and amount of radiation detected by a sensing element of the second optical sensor 432 to a position of the glint 414, a lack of or reduced amount of reflected radiation detected by the sensing element(s) of the second optical sensor 432 may be correlated to the presence and location of the pupil 404 (in the case of so-called "dark-pupil" eye tracking). Thus, when a first portion (e.g., sensing element) of the second optical sensor 432 detects a reduced amount of radiation compared to a second portion (e.g., another sensing element), the eye-tracking system 400 may determine that the pupil 404 (or a greater portion thereof) is positioned within a portion of the FOV 442 associated with the first portion of the second optical sensor 432. Similarly, if a reduced amount of radiation is detected by the second optical sensor 432 compared to by another optical sensor with a different FOV, the eye-tracking system 400 may determine that the pupil 404 (or a greater portion thereof) is at least partially positioned within the FOV 442 associated with the second optical sensor 432.

In some embodiments, one or both of the optical sensors 412, 432 may be used to employ edge detection techniques. Edge detection techniques may involve identifying discontinuities or differences in the radiation (e.g., brightness, amount of radiation, etc.) detected at the sensing elements of the optical sensors 412, 432 for finding the boundaries of objects (e.g., boundaries associated with pupils and/or glints). In some examples, at least one of the optical sensors 412, 432 may be used in conjunction with a comparator to perform edge detection. A comparator may refer to a device that compares two voltages or currents and outputs a signal indicating which of the two voltages or currents is larger. In some examples, a plurality of comparators may be electronically coupled to one or more sensing elements of the optical sensors 412, 432. The comparators may rank the relative intensities of voltages and/or electrical currents produced by the sensing elements to detect edges (e.g., of the glint 414 and/or of the pupil 404).

The comparator may take a variety of different forms, such as a differential comparator (e.g., a comparator that includes a differential amplifier), an operational amplifier-based comparator, a voltage comparator, and/or the like. The comparator may include a continuous comparator or a clocked comparator, which may be operated in a continuous or a clocked fashion, respectively. A continuous comparator may output a signal (e.g., a high or low signal) as a result of an input, such as a voltage or electrical current difference from the sensing elements. The continuous comparator may change its output in near real time to track the state of the input. A clocked comparator (also referred as a latched comparator) may, on the other hand, periodically sample an input and periodically provide corresponding outputs.

In some examples, the comparator may include a digital comparator, which may compare numbers representing two inputs (e.g., voltages or electrical currents from the sensing elements of the optical sensors 412, 432) and may determine whether one number is greater than, less than, or equal to the other number. The digital comparator may output which number is larger. In some examples, a plurality of digital comparators may be electronically coupled to the sensing elements. The digital comparators may be used to rank the relative intensities of voltages and/or currents detected by the sensing elements. This ranking may be performed for determining the relative amount of radiation reaching the individual sensing elements of the optical sensors 412, 432 to determine the position of the glint 414 and/or the pupil 404.

The eye-tracking system 400 is illustrated in FIG. 4 as including the first optical sensor 412 for sensing the glint 414 and the second optical sensor 432 for sensing the pupil 404. However, the present disclosure is not limited to eye-tracking systems 400 that include both types of optical sensors 412, 432. Rather, the present disclosure also includes embodiments in which only optical sensors 412 that detect glints 414 are employed, embodiments in which only optical sensors 432 that detect the pupil 404 are employed, or any combination thereof.

By way of example, FIG. 4 illustrates the modulated radiation 424, 444 as having pulsed waveforms. However, in additional embodiments, the modulated radiation 424, 444 may exhibit other waveforms, such as sinusoidal, triangular, or sawtooth, at varying amplitudes and/or frequencies. The waveform of the modulated radiation 424, 444 may be generated by, for example, an optical modulator, baseband modulation, carrier-based modulation, optical orthogonal frequency-division multiplexing ("O-OFDM"), on-off keying ("OOK"), amplitude-shift keying ("ASK") modulation, and/or pulse position modulation ("PPM"). The modulated radiation 424, 444 may also be encoded with information that can link a light source 416, 436 to a respective optical sensor 412, 432.

In some examples, the substrates of the respective optical sensors 412, 432 may be positioned and/or oriented at predetermined angles to ensure that a sufficient area of potential light reflections may be detected by the optical sensors 412, 432. For example, respective approximate surface normals associated with the substrates may point in parallel directions relative to each other, while the substrates are positioned at a variety of different locations relative to the optical element 408 and/or the frame 410. In another example, the respective approximate surface normals associated with the substrates of the optical sensors 412, 432 may point in non-parallel directions in a predetermined pattern with respect to a viewing angle subtended by the eye 401 relative to the optical sensors 412, 432. In this case, the respective optical sensors 412, 432 may be positioned close to each other, and may still be directed at different portions of the user's eye 401 to cover a wide area of potential locations. Thus, the optical sensors 412, 432, may be positioned and configured to detect respective portions of radiation reflected from the user's eye 401. Depending on the size of the FOVs 422, 442 of the optical sensors 412, 432 (or of sensing elements thereof), a plurality (e.g., from two to thirty-six) of optical sensors 412, 432 may be located in positions and angles such that substantially the entire area of the user's eye 401 may be within the combined fields of view of the optical sensors 412, 432.

The optical sensors 412, 432 may be arrays that include sensing elements that are individually wired with respective amplifiers 418, 438 and/or backend electronics. Additionally or alternatively, the optical sensors 412, 432 may include sensing elements that are grouped and are operably coupled to a collective amplifier 418, 438 and/or backend electronics.

As will be further explained below, one or more of the optical sensors 412, 432 may be relatively low-resolution, and may therefore may include a small number (e.g., from two to about one hundred) respective sensing elements that are relatively large (e.g., at least about 5 μm in both lateral length and lateral width). The low number and/or large size of the sensing elements may enable the eye-tracking system 400 to operate at low power, high speed, and high efficiency compared to conventional high-resolution optical sensors for eye tracking.

By way of example and not limitation, FIGS. 5A and 5B illustrate respective optical sensor arrays 500A and 500B, which may be implemented as any of the optical sensors previously or later described herein. FIG. 5A illustrates a so-called "quad" or "two-by-two" optical sensor array 500A, referring to the number and layout of sensing elements 502A, 502B, 502C, and 502D (collectively referred to as sensing elements 502) making up the optical sensor array 500A. Similarly, FIG. 5B illustrates a so-called "three-by-three" optical sensor array 500B, which is made up of a grid of nine sensing elements 512. However, the present disclosure is not limited to quad or three-by-three optical sensor arrays. Rather, each low-resolution optical sensor used in eye-tracking may include from one to one hundred (e.g., ten-by-ten) sensing elements, for example. Additionally, the optical sensors may have a layout that is square, rectangular, circular, or another configuration. Referring to FIGS. 5A and 5B in conjunction with FIGS. 2 and 3, a plurality of low-resolution optical sensor arrays 500A, 500B may be located at different positions on the HMDs 200, 300 (e.g., as the first optical sensors 216, 308). For example, each of the first optical sensors 216, 308 may include between one and one hundred sensing elements 502, 512, such as in a quad, three-by-three, four-by-four, five-by-five, six-by-six, and/or ten-by-ten configuration.

Referring again to FIGS. 5A and 5B, the sensing elements 502, 512 may be or include any element that produces an output in response to exposure to radiation. The sensing elements 502, 512 may be sensitive to certain wavelengths of radiation (e.g., infrared radiation, near-infrared radiation, visible radiation, a subset or combination thereof, etc.). By way of example and not limitation, the sensing elements 502, 512 may be or include at least one of: a charge-coupled device ("CCD") sensor, a complementary metal-oxide-semiconductor ("CMOS") sensor, and/or a photodiode sensor. In addition, the sensing elements 502, 512 may be configured to detect a waveform of radiation (e.g., modulated radiation) reflected off the user's eye for determining a source of the reflected radiation, as discussed herein.

Referring to FIG. 5A, the quad optical sensor array 500A may include a two-by-two grid of the sensing elements 502. Each of the sensing elements 502 may be square in shape as shown in FIG. 5A, although other shapes (e.g., circular, rectangular, etc.) are also contemplated and included in the present disclosure. Each of the sensing elements 502 may have a lateral length L and a lateral width W. In some examples, the lateral length L and the lateral width W may each be at least about 5 μm, such as about 10 μm, about 14 μm, about 20 μm, or larger. Conventional sensing elements that may be used in eye-tracking may be substantially smaller, such as having a lateral length and a lateral width of about 2.5 μm or less (e.g., about 1 μm). The relatively larger sensing elements 502 of the present disclosure may enable the collection of more light per sensing element 502, which may reduce an SNR and may increase light sensitivity compared to conventional sensing elements. In addition, a relatively fewer number of relatively larger sensing elements 502 may increase a computing speed and reduce power for analyzing data from the sensing elements 502. Of course, concepts of the present disclosure may also be implemented with high-resolution optical sensors, and may not be limited to implementation with low-resolution optical sensors.

In FIG. 5A, a projection 504 (e.g., of a glint or of a pupil) may be substantially centered on the optical sensor array 500A. Thus, substantially equal portions of radiation (or lack thereof) corresponding to the projection 504 may be detected by each of the sensing elements 502A, 502B, 502C, and 502D of the optical sensor array 500A. Because of the substantially equal portions of radiation, respective outputs of the sensing elements 502A, 502B, 502C, and 502D may also be substantially equal. Therefore, an eye-tracking system utilizing the optical sensor array 500A may analyze the outputs from the sensing elements 502 to determine that the projection 504 is substantially centered on the optical sensor array 500A and may then correlate the position of the projection 504 to a position of the user's eye.

In some embodiments, the projection 504 may be focused or defocused on the optical sensor array 500A, such that a size of the projection 504 spans at least one of the sensing elements 502. For example, if a glint or other projection 504 does not span at least one of the sensing elements 502, then it may be difficult to determine where within the sensing element 502 the glint or other projection 504 is located. Accordingly, the optics (e.g., the micro-lenses 420, 440 of FIG. 4) may be selected, tailored, or adjusted to focus or defocus the projection 504 for improved accuracy of eye tracking.

Referring to FIG. 5B, the three-by-three optical sensor array 500B may include nine sensing elements 512, including sensing elements 512A, 512B, 512C, and 512D. A projection 514 (e.g., of a glint or of a pupil) may be positioned over respective portions of the sensing elements 512A, 512B, 512C, and 512D. By way of illustration and example, a largest portion of the projection 514 may be positioned over the sensing element 512A and a smallest portion of the projection 514 may be positioned over the sensing element 512D. Substantially equal, intermediate portions of the projection 514 may be positioned over the sensing elements 512B and 512C. The projection 514 may not be positioned over other sensing elements 512 of the optical sensor array 500B. By comparing the amount of light reaching the sensing elements 512A, 512B, 512C, and 512D, and the other sensing elements 512, an eye-tracking system utilizing the optical sensor array 500B may analyze the outputs from the sensing elements 502 to determine the position of the projection 514 and a corresponding position of the user's eye.

In some embodiments, optical sensors of the present disclosure may be or include a position-sensing detector (a "PSD", such as a lateral effect PSD). A PSD may include a single photosensitive sensing element or an array of multiple (e.g., two, four, etc.) sensing elements. In the case of a PSD with a single sensing element, the PSD may also include at least three electrodes. One of the electrodes may serve as a common electrode and the other two electrodes may respectively include a first position-sensing electrode and a second position-sensing electrode at two different locations on the sensing element. Light (e.g., infrared or visible light from a glint reflected off the user's eye) that is absorbed by the single sensing element closer to the first electrode than the second electrode may induce a greater signal (e.g., a change in voltage or current, or both) in the first electrode compared to the second electrode. In additional embodiments, a PSD with a single sensing element may include a common electrode and three or four position-sensing electrodes connected thereto, such as for increased sensitivity and improved accuracy of position determination.

FIG. 6 shows an example optical sensor 600 and associated backend electronics 610 for eye tracking. The optical sensor 600 may include an array of photosensitive sensing elements 602 or a single photosensitive sensing element 602. For ease of illustration, FIG. 6 shows the optical sensor 600 having four sensing elements 602, but embodiments of the present disclosure are not so limited. For example, the optical sensor 600 may include a single sensing element, 3 by 3 array, a 4 by 4 array, a 5 by 5 array, a 6 by 6 array, a 10 by 10 array, a 2 by 1 array, a 3 by 1 array, a 3 by 2 array, or any size or arrangement of sensing elements. The optical sensor 600 may include one or more traces 608 and/or buses which may bias, transmit, and/or detect signals from the sensing elements 602. By way of example and not limitation, the sensing elements 602 of the optical sensor 600 may be CCD sensing elements, CMOS sensing elements, a PSD sensing element, and/or photodiode sensing elements.

The sensing elements 602 may (individually or as a group) be driven, controlled, and/or read by backend electronics 610. The backend electronics 610 may be physically positioned adjacent to (e.g., beneath) the sensing elements 602 or may be positioned remotely (e.g., on or in the frame, temple components, a separate wearable device, a connected computer, and/or the like) relative to the optical sensor 600. In some examples, the backend electronics 610 may be operably coupled to the sensing elements 602 via the traces 608. The optical sensor 600 may be connected to multiple backend electronics components, such as a combination of lock-in amplifiers and/or operational amplifiers to measure, for example, signals from individual and/or aggregate signals resulting from radiation reaching the optical sensor 602.

The backend electronics 610 may be configured to determine that an artifact such as a portion of the eye (e.g., eyelashes) has blocked a particular light source and/or the sensing elements of the optical sensor 600 during eye tracking procedures. For example, the backend electronics 610 may filter signals detected by the optical sensor 600 from the light source(s). The background electronics 610 may be used to turn off, filter out, and/or discard signals generated by the optical sensor 600 or modulated radiation generated by the light source(s). This may save computational resources that would have been otherwise used in generating and/or processing erroneous, empty, or superfluous data.

The backend electronics 610 may include, for example, one or more of: a passive filter 612, an active filter 614, and/or a processor 616. The passive filter 612 may be, for example, a linear filter including a combination of resistors R, inductors L, and/or capacitors C. These components of the passive filter 612 may not depend upon an external power supply and/or they may not contain active components (e.g., transistors, amplifiers, and/or the like). In the example shown in FIG. 6, the passive filter 612 may include an inductor L, which may function to block high-frequency signals while conducting low-frequency signals. Thus, the passive filter 612 may be or include a low-pass filter in which the inductor L provides a path for the signal to ground, such as to provide lower attenuation to low-frequency signals than to high-frequency signals. Conversely, the passive filter 612 may include a capacitor C, which may function to conduct high-frequency signals while blocking low-frequency signals. The passive filter 612 may also include a resistor R in combination with the inductor L and/or the capacitor C. The resistor R may not have a frequency-selective property. The resistor R or the combination of the inductor L and capacitor C may be included to tune various circuit time constraints and, therefore, the frequencies to which the passive filter 612 responds. Thus, the passband of the passive filter 612 may be tuned, such as to filter out noise from the optical sensor 600.

While a three-element RLC-type passive filter 612 is depicted in FIG. 6, the disclosure is not so limited. Rather, in some embodiments, the passive filter 612 may include a single-element filter, a two-element filter, or the three-element filter. For example, the passive filter 612 may include an RC circuit, an RL circuit, and/or an LC circuit to perform any suitable filtering step.

The active filter 614 may be or include an active component, such as an amplifier to amplify signals from the sensing elements 602. For example, the active filter 614 may be or include an operational amplifier, which may have a relatively high quality factor ("Q factor") and may include resonance modes without the use of inductors.

The processor 616 may be or include a digital computational component that may perform operations (e.g., mathematical or comparative operations) on the signals from the sensing elements. The operations may be performed to reduce or enhance certain aspects of the signals, such as to reduce or remove noise, to reduce or remove signal components corresponding to artifacts, to increase or amplify signals having a predetermined characteristic (e.g., corresponding to modulated radiation), and/or the like. The processor 616 may include a microprocessor and other peripheral components (e.g., memory) to process and store data and operational results. The processor 616 may include corresponding computer-executable instructions to, for example, implement a digital filter by performing operations on signals from the optical sensor 600.

The processor 616 may be or include an application-specific integrated circuit ("ASIC"), a field-programmable gate array ("FPGA"), or other component for implementing a filtering and/or computational operation on the signals. In some examples, the processor 616 may be configured to perform a fast Fourier transform ("FFT") on the signals to alter a domain associated with the signal. In some examples, an FFT may refer to an algorithm that may compute a discrete Fourier transform ("DFT") or an inverse discrete Fourier transform ("IDFT") on the signals from the optical sensor 600 to identify certain frequencies associated with the modulated radiation detected by the sensing elements 602.

The backend electronics 610 may be grounded. In some examples, the backend electronics 610 may include a common ground 618 for all sensing elements 602 thereof, or may include a separate ground for one or more sensing elements 602 of the optical sensor 600.

FIG. 7 shows a schematic diagram of an example amplifier system 700 that may be used in connection with the optical sensors of the present disclosure, such as to remove noise to extract a signal associated with detected modulated radiation. By way of example and not limitation, the amplifier system 700 may be implemented as the first amplifier 418 and/or second amplifier 438 of FIG. 4, discussed above. The amplifier system 700 may be or include a so-called "lock-in amplifier."

The amplifier system 700 may include a first voltage input 702 that may be fed into a signal amplifier 704 (e.g., an alternating current ("AC") amplifier), which may include a voltage amplifier combined with variable filters. A second voltage input 703 may be fed into an oscillator 706 (e.g., a voltage-controlled oscillator ("VCO")), which may include an oscillator that can synchronize with an external reference signal (e.g., trigger), for example, in phase and/or frequency. Alternatively, the oscillator 706 may be configured to operate without an external reference. In some examples, the oscillator 706 may include a phase-shifting circuit that may be configured to shift a phase of the signal by a predetermined amount (e.g., from 0 to 360 degrees) with respect to a reference signal.

The amplifier system 700 may monitor a voltage of an output 708 of the signal amplifier 704 by taking a reading at the output 708 of the signal amplifier 704. Similarly, the amplifier system 700 may monitor a voltage of an output 710 of the oscillator 706 by taking a reading at the output 710 of the oscillator 706.

The amplifier system 700 may also include a multiplier 707, such as a phase-sensitive detector ("PSD"). The multiplier 707 may take in two voltages (e.g., respectively from the signal amplifier 704 and the oscillator 706) and may produce an output that is the product of the two voltages. A low-pass filter 712 may be coupled to an output of the multiplier 707. The low-pass filter 712 may be, for example, a passive filter (e.g., an RC filter), to allow portions of the signal that have a relatively low frequency to pass.

A direct current ("DC") filter 714 may follow the low-pass filter 712 in the amplifier system 700. The DC filter 714 may include, for example, a low-frequency amplifier. The amplifier system 700 may provide an output voltage 716 at the output of the DC filter 714. The output voltage 716 may be a stronger signal and may exhibit reduced noise compared to a signal input into the amplifier system 700 from an optical sensor or a sensing element thereof.

For example, the amplifier system 700 may use a reference signal at the approximate frequency of the signal to be extracted (e.g., at a frequency associated with modulated radiation from a light source). The amplifier system 700 may output a signal (e.g., the output voltage 716) in which the contributions of all signals (including noise) not at the reference frequency may be attenuated at or close to zero. Therefore, the amplifier system 700 may output a DC signal that is proportional to the strength of the original input signal at the reference frequency.

In additional embodiments, the amplifier system 700 may include a homodyne detector followed by an adjustable low-pass filter. Further, the amplifier system 700 may use analog frequency mixers and RC filters for signal demodulation. The amplifier system 700 may use digital components to perform digital signal processing on the inputted noisy signals.

FIG. 8A shows a plot 800A of an unprocessed signal of an optical sensor without the use of an amplifier system, such as the amplifier system 700 described above with reference to FIG. 7. FIG. 8B shows a plot 800B of a signal of an optical sensor with the use of an amplifier system, such as the amplifier system 700 described above with reference to FIG. 7.

A curve 806 of the plot 800A may indicate a number of peaks in the signal at a variety of frequencies. The peaks in the signal may include peaks that correspond to modulated radiation emitted by light sources and sensed by the optical sensor as well as peaks that correspond to noise (e.g., radiation from other sources). For example, the modulated radiation emitted by light sources may be produced at certain respective frequencies $f_1$, $f_2$, $f_3$, and $f_4$. However, the noise associated with the signal and the resulting curve 806 may make it difficult to identify the strength (e.g., relative strength) of the signals associated with the modulated radiation at the respective frequencies $f_1$, $f_2$, $f_3$, and $f_4$.

In contrast, a curve 816 of the plot 800B, which may result from passing a signal through the amplifier system 700 of FIG. 7, may more distinctly indicate peaks 820, 822, 824, and 826 in and relative strengths of the signal at the respective frequencies $f_1$, $f_2$, $f_3$, and $f_4$. Thus, use of the amplifier system 700 of FIG. 7 may facilitate analysis of a signal from an optical sensor.

FIG. 9A is a schematic illustration of an example optical sensing system 900. FIG. 9B is a plot 902 showing an example voltage output of the optical sensing system 900 of FIG. 9A over time.

Referring to FIG. 9A, the optical sensing system 900 may include a sensing element 904, which may be an event-based or event-driven sensing element 904 that is configured to react to local illumination changes in substantially real time. The sensing element 904 may produce an electrical signal in response to incident radiation 906 and/or in response to a change in the incident radiation 906 (e.g., a change in intensity of the incident radiation 906). An output of the sensing element 904 may be operably coupled to a log block 908, which may be sensitive to the natural logarithm of a current generated and output by the sensing element 904. An output of the log block 908 may be operably coupled to a capacitor 910, which may balance the output of a connected amplifier 912 (e.g., an inverting amplifier) to a preset level. For example, the gain of the amplifier 912 may be determined at least in part by the capacitor 910. A first filter 914 and a second filter 916 may be operably coupled to an output of the amplifier 912. The first filter 914 may be configured to detect an "ON" state of the sensing element 904, and the second filter 916 may be configured to detect an "OFF" state of the sensing element 904. For example, when the signal output by the amplifier 912 increases past a predetermined threshold, an "ON" event may be detected and/or generated by the first filter 914. Conversely, when the signal output by the amplifier decreases past a predetermined threshold, an "OFF" event may be detected and/or generated by the second filter 916.

For example, referring to FIG. 9B, a curve 918 representing voltages in the optical sensing system 900 of FIG. 9A is shown. First data points 920 (represented by parallel hatching in FIG. 9B) correspond to "ON" states of the optical sensing system 900. The first data points 920 are present when the voltage rises by a predetermined amount. Second data points 922 (represented by cross hatching in FIG. 9B) correspond to "OFF" states of the optical sensing system 900. The second data points 922 are present when the voltage falls by a predetermined amount. The "ON" and "OFF" states may be utilized by the optical sensing system 900 for event-driven analysis and processing, which may be more efficient than a similar conventional optical sensing system that may continuously monitor corresponding sensing elements. For example, the event-driven optical sensing system 900 may provide lower latency and higher temporal resolution than conventional (i.e., non-event-driven) cameras. The optical sensing system 900 may reduce a delay associated with input changes and may provide a higher dynamic range compared with conventional cameras. In addition, the optical sensing system 900 may utilize a lower bandwidth than conventional cameras, such as by only using bandwidth when changes in illumination are detected and not when the illumination is constant.

FIG. 10 is a flow chart illustrating a method 1000 for eye tracking. At operation 1002, at least one light source may emit modulated radiation toward a user's eye. The radiation may be modulated in a manner that enables the light source to be identified, such as by detection and analysis of the modulated radiation. Operation 1002 may be performed in a variety of ways. For example, as described above, the light source may be configured to emit radiation (e.g., infrared radiation, visible radiation, etc.) that has a predetermined waveform, such as a predetermined frequency, amplitude, and/or phase. In some embodiments, a plurality of light sources may emit radiation that is respectively modulated in different manners, such that each of the light sources emits radiation having a unique and identifiable waveform.

At operation 1004, at least a portion of the modulated radiation reflected off the user's eye may be detected by at least one optical sensor, which may include at least one sensing element. Operation 1004 may be performed in a variety of ways. In some examples, the optical sensor may include one or more event-driven sensing elements, as described above in connection with FIGS. 9A and 9B. In additional examples, the sensing elements may be or include CCD sensing elements, CMOS sensors, PSD sensors, and/or photodiode sensors. In some embodiments, the method 1000 may also including determining that the optical sensor (or a sensing element thereof) has stopped receiving at least a portion of the modulated radiation emitted by the identified light source. For example, the optical sensor or a portion thereof may be blocked by an artifact such as an eyelash or eyelid of the user's eye. Accordingly, signals corresponding to the optical sensor may be turned off or disregarded to improve an efficiency of the associated eye-tracking system. In addition, the modulated radiation may be filtered, such as by one of the passive or active filters described above. In further embodiments, the signal generated by the optical sensor may be amplified, such as by one of the amplifiers described above.

At operation 1006, the light source that emitted the modulated radiation reflected off the user's eye and detected by the optical sensor may be identified (e.g., uniquely identified). A processor may perform the identification of the light source. Operation 1006 may be performed in a variety of ways. For example, a signal from the optical sensor corresponding to the modulated radiation may be processed, such as to reduce or remove noise in the signal, and the signal may be converted (e.g., via a FFT operation) and/or analyzed to determine one or more peak frequencies, phases, and/or amplitudes to identify how the radiation is modulated, as discussed above. This information may be correlated by the processor to one of the light sources from which the modulated radiation originated.

FIG. 11 is schematic illustration of an example display system (e.g., an HMD) 1100, which may be capable of tracking a position of a user's eye 1101. The display system 1100 may include one or more light sources 1102, an optical subsystem 1104, an eye-tracking subsystem 1106, and/or a control subsystem 1108.

The light source(s) 1102 may generate light 1110 (e.g., modulated light, as discussed above) that may be directed toward the user's eye 1101 for eye-tracking purposes. For example, the light source(s) 1102 may include any device(s) capable of producing such light 1110, such as at least one IRED. The light 1110 for eye-tracking may be structured (e.g., having a predetermined pattern, such as a grid or other shape), unstructured (e.g., a field of substantially continuous illumination), or in one or more points (e.g., glints). Reflected light 1112 may reflect off the user's eye 1101 and may be detected by the eye-tracking subsystem 1106.

The eye-tracking subsystem 1106 may include a plurality of optical sensors, which may include a low-resolution optical sensor and/or a high-resolution optical sensor, as described above. The optical sensors may be configured to detect the light 1110 and identify modulated radiation signals thereof. The eye-tracking subsystem 1106 may be configured to determine a position, motion, and gaze distance/angle of the user's eye 1101. The eye-tracking subsystem 1106 may also be configured to identify a particular light source 1102 associated with a given signal corresponding to modulated radiation from the light 1110.

In additional embodiments, the light source(s) 1102 may produce an image 1114 (e.g., video content, artificial-reality content, etc.) displayed to the user's eye 1101 by the display system 1100. For example, the light source(s) 1102 may include a two-dimensional ("2D") projector (e.g., a LCoS display), a scanning source (e.g., a scanning laser), or another electronic display device (e.g., a LCD, an LED display, an OLED display, an active-matrix OLED display (AMOLED), a transparent OLED display (TOLED), or some other display) that is capable of generating light for presenting the image 1114 to the user. In some embodiments, the light source 1102 may pass the image 1114 (e.g., a virtual image) through the optical subsystem 1104. The optical subsystem 1104 may include, for example, an optical lens configured to cause light containing the image 1114 to converge at or near a pupil 1116 of the user's eye 1101. In some examples, the optical subsystem 1104 may include any number of lenses (e.g., Fresnel lenses, convex lenses, concave lenses), apertures, filters, mirrors, prisms, and/or other optical components, possibly in combination with actuators and/or other devices. For example, the actuators and/or other devices may translate and/or rotate one or more of the optical components to alter one or more aspects of the image 1114. Further, various mechanical couplings may serve to maintain the relative spacing and/or the orientation of the optical components in any suitable combination.

The control subsystem 1108 may include one or more processors, which may be configured to control one or more of the light source(s) 1102, the optical subsystem 1104, and/or the eye-tracking subsystem 1106. In some examples, the control subsystem 1108 may control the light source(s) 1102 and/or the optical subsystem 1104 based on data from the eye-tracking subsystem 1106. Additionally, in some examples, the control subsystem 1108 may store and utilize historical tracking information (e.g., a history of the tracking information over a given duration, such as the previous second or fraction thereof) to anticipate the gaze angle of the eye 1101 (e.g., an angle between a visual axis and an anatomical axis of the eye 1101). In some embodiments, the eye-tracking subsystem 1106 may detect radiation emanating from (e.g., reflected from) some portion of the eye 1101 (e.g., the cornea, the iris, the pupil, or the like) to determine the current gaze angle of the eye 1101. In other examples, the eye-tracking subsystem 1106 may employ a wavefront sensor to track the current location of the pupil.

Any number of techniques can be used to track the eye 1101. Some techniques may involve illuminating the eye 1101 with infrared light (e.g., from the light source(s) 1102) and measuring reflections with at least one optical sensor (e.g., of the eye-tracking subsystem 1106) that is tuned to be sensitive to the infrared light. Information about how the infrared light 1110 is reflected from the eye 1101 (including how modulated radiation reflects from the eye 1101) may be analyzed to determine the position(s), orientation(s), and/or motion(s) of one or more feature(s) of the eye 1101, such as the cornea, pupil, iris, and/or retinal blood vessels. In some examples, the radiation captured by a sensing element of the eye-tracking subsystem 1106 may be digitized (i.e., converted to an electronic signal). Further, the sensing element may transmit a digital representation of this electronic signal to one or more processors (for example, processors associated with a device including the eye-tracking subsystem 1106).

In some examples, one or more processors may process the digital representation generated by the sensing element(s) of the eye-tracking subsystem 1106 to track the movement of the eye 1101. In another example, these processors may track the movements of the eye 1101 by executing algorithms represented by computer instructions stored on non-transient memory. In some examples, on-chip logic (e.g., an application-specific integrated circuit, ASIC) may be used to perform at least portions of such algorithms.

As noted, the eye-tracking subsystem 1106 may be programmed to use an output of the sensing element(s) to track movement of the eye 1101. In some embodiments, the eye-tracking subsystem 1106 may analyze the digital representation generated by the sensors to extract eye rotation information from changes in reflections. In one embodiment, the eye-tracking subsystem 1106 may use corneal reflections or glints and/or the center of the eye's pupil 1116 as features to track over time, as discussed above with reference to FIGS. 4, 5A, and 5B.

In some embodiments, the eye-tracking subsystem 1106 may use two types of infrared and/or near-infrared (also known as active light) eye-tracking techniques: bright-pupil and dark-pupil eye tracking, which may be differentiated based on the location of the light source(s) 1102 with respect to the optical elements used. If the illumination is coaxial with the optical path, then the eye 1101 may act as a retroreflector as the incident light 1110 reflects off the retina, thereby creating a bright pupil effect similar to a red eye effect in photography. If the light source(s) 1102 is/are offset from the optical path, then the pupil 1116 may appear dark because the retroreflection from the retina is directed away from the sensor. In some embodiments, bright-pupil tracking may create greater iris/pupil contrast, allowing more robust eye tracking with iris pigmentation, and may feature reduced interference (e.g., interference caused by eyelashes and other obscuring features). Bright-pupil tracking may also allow tracking in lighting conditions ranging from total darkness to a very bright environment.

In some embodiments, the control subsystem 1108 may control the light source(s) 1102 and/or the optical subsystem 1104 to reduce optical aberrations (e.g., chromatic aberrations and/or monochromatic aberrations) of the image 1114 that may be caused by or influenced by the eye 1101 of the viewer. In some examples, as mentioned above, the control subsystem 1108 may use the tracking information from eye-tracking subsystem 1106 to perform such controls. For example, in controlling the light source(s) 1102 (e.g., to provide modulated radiation from the light source(s) 1102), the control subsystem 1108 may alter the light generated by the light source(s) 1102 (e.g., by way of image rendering) to modify (e.g., pre-distort) the image 1114 so that the aberration of the image 1114 caused by eye 1101 may be reduced or eliminated.

The disclosed systems may track both the position and relative size of the pupil (since, e.g., the pupil dilates and/or contracts). In some examples, the eye-tracking devices and components (e.g., sensors and/or sources) used for detecting and/or tracking the pupil may be different (or calibrated differently) for different types of eyes. For example, the frequency range of the sensors may be different (or separately calibrated) for eyes of different colors and/or different pupil types, sizes, and/or the like. As such, the various eye-tracking components (e.g., infrared sources and/or sensors) described herein may need to be calibrated for each individual user and/or eye.

The disclosed systems may track both eyes with and without ophthalmic correction, such as contact lenses worn by the user. In some embodiments, ophthalmic correction elements (e.g., adjustable lenses) may be directly incorporated into the display system (e.g., HMD). In some examples, the eye-tracking algorithm(s) may be modified based on the color of the user's eye. For example, eye-tracking algorithm(s) may be modified based at least in part on the differing color contrast between a brown eye and, for example, a blue eye.

Embodiments of the present disclosure may provide for improved eye tracking. For example, emitting modulated radiation from light sources may enable the unique identification the respective light sources, to reduce the effects of noise and facilitate processing of signals from optical sensors. In addition, the accuracy and speed of eye tracking may be improved using the concepts of the present disclosure.

As noted, the disclosed systems may use various AI-based algorithms and techniques for carrying out the various embodiments and/or examples disclosed herein. These AI-based algorithms and techniques may provide for or aid in the numerous determinations (e.g., to determine, identify, ascertain, infer, calculate, predict, prognose, estimate, derive, forecast, detect, compute, etc.) described herein. For example, the components described herein can examine the entirety or a subset of the data to which it is granted access and can provide reasoning about or determine states of the system, environment, etc. from a set of observations, as captured via events and/or data. Determinations can be employed to identify a specific context or action to generate, for example, a probability distribution over states. In one example, these determinations may be probabilistic; that is, they may involve the computation of a probability distribution over states of interest based on a consideration of data and events. These determinations can also refer to techniques employed for composing higher-level events from a set of events and/or data.

Such determinations can result in the construction of new events or actions from a set of observed events and/or stored event data, whether the events are correlated in close temporal proximity and/or whether the events and data originate from one or several event and/or data sources (e.g., different sensor inputs). The systems and components disclosed herein may also employ various classifications, both explicitly trained (e.g., via training data) and implicitly trained (e.g., via observing behavior, preferences, historical information, receiving extrinsic information, etc.), schemes, and/or systems (e.g., support vector machines, neural networks, expert systems, Bayesian belief networks, fuzzy logic, data fusion engines, etc.) when performing the automatic and/or determined actions disclosed herein. As such, the disclosed systems may use classification schemes and/or systems to automatically learn and/or perform a variety of functions, actions, and/or determinations For example, a classifier may map an input attribute vector, z=(z1, z2, z3, z4, . . . , zn) to a confidence that the input belongs to a class, as represented by f(z)=confidence (class). Such classifications can employ a probabilistic and/or statistical-based analysis (e.g., factoring into the analysis utilities and costs) to determinate an action to be automatically performed. A support vector machine (SVM) is one example of such a classifier. This SVM may operate by finding a hyper-surface in the space of possible inputs, where the hyper-surface attempts to split the triggering criteria from the non-triggering events. This may make the classification correct for testing data that is near, but not identical to training data. Other directed and undirected model classification approaches include, for example, naïve Bayes and Bayesian networks, decision trees, neural networks, fuzzy logic models, and/or probabilistic classification models providing different patterns of independence.

As detailed above, embodiments of the present disclosure may include or be implemented in conjunction a cloud-computing system. Cloud computing can refer to a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. A cloud-computing environment may include one or more cloud computing nodes with which local computing devices used by cloud consumers (such as personal digital assistants or cellular phones, desktop or laptop computers, and/or automobile computer systems) can communicate. In a cloud-computing system, nodes can communicate with one another. They can be grouped physically or virtually, in one or more networks, such as private, community, public, or hybrid clouds. This allows cloud-computing environment to offer infrastructure, platforms, and/or software as services for which a cloud consumer does not need to maintain resources on a local computing device. In some examples, a cloud-computing system can communicate with any type of computerized device over any type of network and/or network-addressable connection (using, e.g., a web browser).

Embodiments of the present disclosure may include or be implemented in conjunction with various types of artificial-reality systems. Artificial reality is a form of reality that has been adjusted in some manner before presentation to a user, which may include, e.g., a virtual reality, an augmented reality, a mixed reality, a hybrid reality, or some combination and/or derivative thereof. Artificial-reality content may include completely generated content or generated content combined with captured (e.g., real-world) content. The artificial-reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, e.g., create content in an artificial reality and/or are otherwise used in (e.g., to perform activities in) an artificial reality.

Artificial-reality systems may be implemented in a variety of different form factors and configurations. Some artificial-reality systems may be designed to work without near-eye displays (NEDs), an example of which is augmented-reality system 1200 in FIG. 12. Other artificial-reality systems may include an NED that also provides visibility into the real world (e.g., augmented-reality system 1300 in FIG. 13) or that visually immerses a user in an artificial reality (e.g., virtual-reality system 1400 in FIG. 14). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Figure 12:
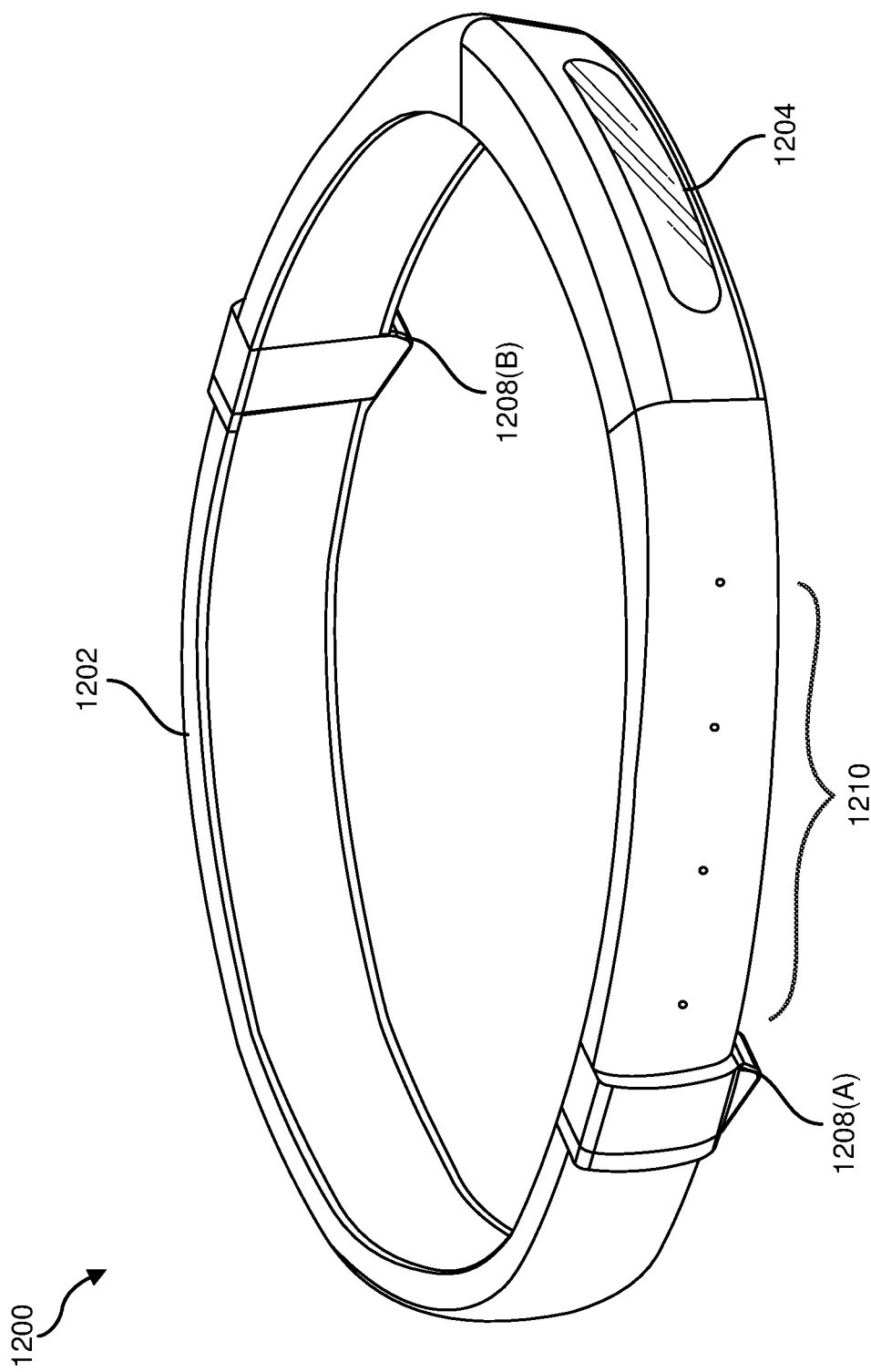
FIG. 12 is an illustration of an example artificial-reality headband that may be used in connection with embodiments of this disclosure.

Turning to FIG. 12, the augmented-reality system 1200 generally represents a wearable device dimensioned to fit about a body part (e.g., a head) of a user. As shown in FIG. 12, system 1200 may include a frame 1202 and a camera assembly 1204 that is coupled to frame 1202 and configured to gather information about a local environment by observing the local environment. The augmented-reality system 1200 may also include one or more audio devices, such as output audio transducers 1208(A) and 1208(B) and input audio transducers 1210. The output audio transducers 1208(A) and 1208(B) may provide audio feedback and/or content to a user, and the input audio transducers 1210 may capture audio in a user's environment.

As shown, the augmented-reality system 1200 may not necessarily include an NED positioned in front of a user's eyes. Augmented-reality systems without NEDs may take a variety of forms, such as head bands, hats, hair bands, belts, watches, wrist bands, ankle bands, rings, neckbands, necklaces, chest bands, eyewear frames, and/or any other suitable type or form of apparatus. While the augmented-reality system 1200 may not include an NED, the augmented-reality system 1200 may include other types of screens or visual feedback devices (e.g., a display screen integrated into a side of the frame 1202).

Figure 13:
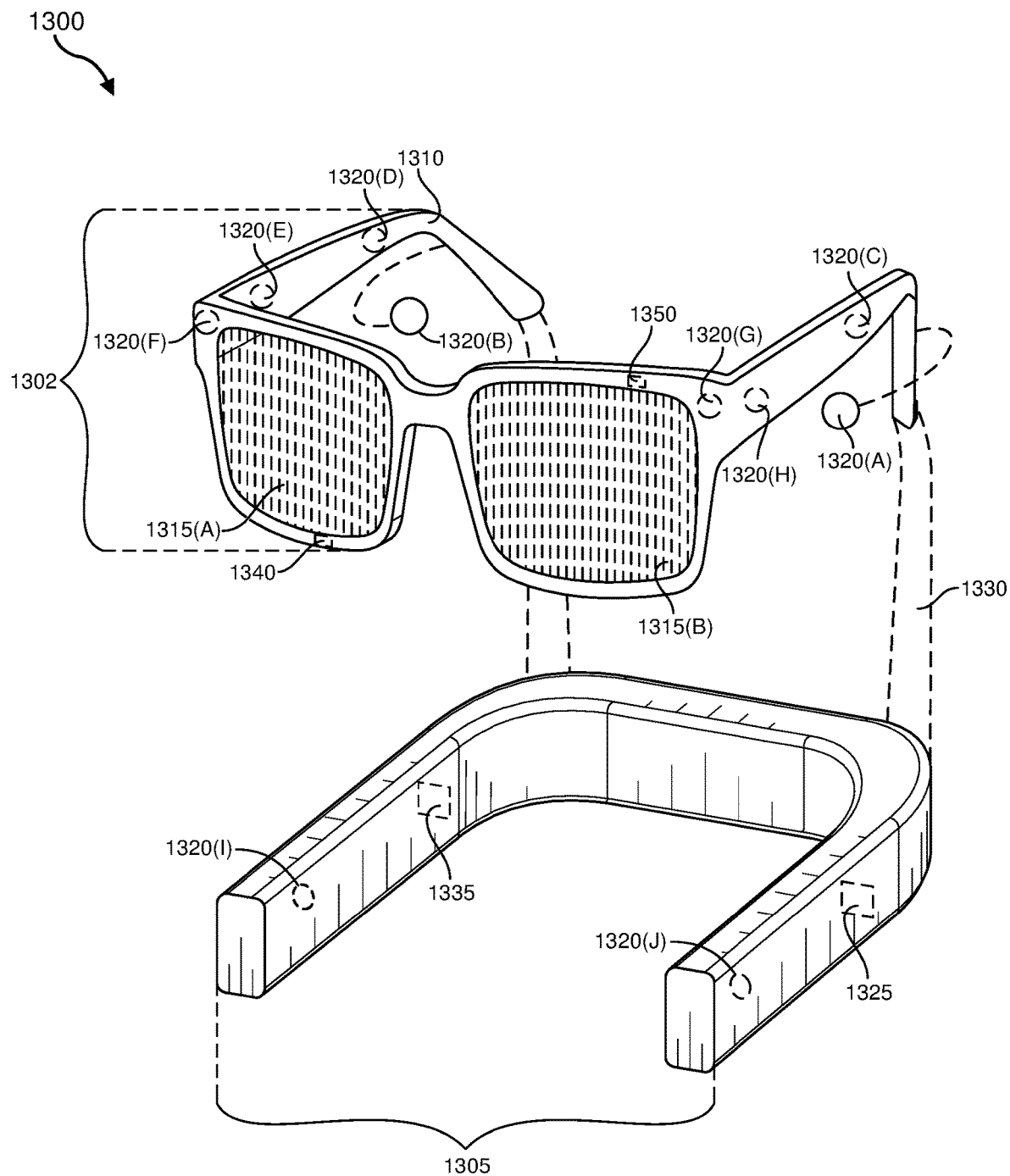
FIG. 13 is an illustration of example augmented-reality glasses that may be used in connection with embodiments of this disclosure.

The embodiments discussed in this disclosure may also be implemented in augmented-reality systems that include one or more NEDs. For example, as shown in FIG. 13, the augmented-reality system 1300 may include an eyewear device 1302 with a frame 1310 configured to hold a left display device 1315(A) and a right display device 1315(B) in front of a user's eyes. The display devices 1315(A) and 1315(B) may act together or independently to present an image or series of images to a user. While the augmented-reality system 1300 includes two displays, embodiments of this disclosure may be implemented in augmented-reality systems with a single NED or more than two NEDs.

In some embodiments, the augmented-reality system 1300 may include one or more sensors, such as a sensor 1340. The sensor 1340 may generate measurement signals in response to motion of the augmented-reality system 1300 and may be located on substantially any portion of the frame 1310. The sensor 1340 may represent a position sensor, an inertial measurement unit (IMU), a depth camera assembly, or any combination thereof. In some embodiments, the augmented-reality system 1300 may or may not include the sensor 1340 or may include more than one sensor. In embodiments in which the sensor 1340 includes an IMU, the IMU may generate calibration data based on measurement signals from the sensor 1340. Examples of the sensor 1340 may include, without limitation, accelerometers, gyroscopes, magnetometers, other suitable types of sensors that detect motion, sensors used for error correction of the IMU, or some combination thereof.

The augmented-reality system 1300 may also include a microphone array with a plurality of acoustic transducers 1320(A)-1320(J), referred to collectively as acoustic transducers 1320. The acoustic transducers 1320 may be transducers that detect air pressure variations induced by sound waves. Each acoustic transducer 1320 may be configured to detect sound and convert the detected sound into an electronic format (e.g., an analog or digital format). The microphone array in FIG. 2 may include, for example, ten acoustic transducers: 1320(A) and 1320(B), which may be designed to be placed inside a corresponding ear of the user, acoustic transducers 1320(C), 1320(D), 1320(E), 1320(F), 1320(G), and 1320(H), which may be positioned at various locations on frame 1310, and/or acoustic transducers 1320(1) and 1320(J), which may be positioned on a corresponding neckband 1305.

In some embodiments, one or more of the acoustic transducers 1320(A)-(F) may be used as output transducers (e.g., speakers). For example, the acoustic transducers 1320 (A) and/or 1320(B) may be earbuds or any other suitable type of headphone or speaker.

The configuration of the acoustic transducers 1320 of the microphone array may vary. While the augmented-reality system 1300 is shown in FIG. 13 as having ten acoustic transducers 1320, the number of acoustic transducers 1320 may be greater or less than ten. In some embodiments, using higher numbers of acoustic transducers 1320 may increase the amount of audio information collected and/or the sensitivity and accuracy of the audio information. In contrast, using a lower number of the acoustic transducers 1320 may decrease the computing power required by an associated controller 1350 to process the collected audio information. In addition, the position of each acoustic transducer 1320 of the microphone array may vary. For example, the position of an acoustic transducer 1320 may include a defined position on the user, a defined coordinate on the frame 1310, an orientation associated with each acoustic transducer 1320, or some combination thereof.

The acoustic transducers 1320(A) and 1320(B) may be positioned on different parts of the user's ear, such as behind the pinna or within the auricle or fossa. Or, there may be additional acoustic transducers on or surrounding the ear in addition to the acoustic transducers 1320 inside the ear canal. Having an acoustic transducer 1320 positioned next to an ear canal of a user may enable the microphone array to collect information on how sounds arrive at the ear canal. By positioning at least two of the acoustic transducers 1320 on either side of a user's head (e.g., as binaural microphones), the augmented-reality device 1300 may simulate binaural hearing and capture a 3D stereo sound field around about a user's head. In some embodiments, the acoustic transducers 1320(A) and 1320(B) may be connected to the augmented-reality system 1300 via a wired connection 1330, and in other embodiments, the acoustic transducers 1320(A) and 1320(B) may be connected to the augmented-reality system 1300 via a wireless connection (e.g., a Bluetooth connection). In still other embodiments, the acoustic transducers 1320(A) and 1320(B) may not be used at all in conjunction with the augmented-reality system 1300.

The acoustic transducers 1320 on the frame 1310 may be positioned along the length of the temples, across the bridge, above or below the display devices 1315(A) and 1315(B), or some combination thereof. The acoustic transducers 1320 may be oriented such that the microphone array is able to detect sounds in a wide range of directions surrounding the user wearing the augmented-reality system 1300. In some embodiments, an optimization process may be performed during manufacturing of the augmented-reality system 1300 to determine relative positioning of each acoustic transducer 1320 in the microphone array.

In some examples, the augmented-reality system 1300 may include or be connected to an external device (e.g., a paired device), such as the neckband 1305. The neckband 1305 generally represents any type or form of paired device. Thus, the following discussion of the neckband 1305 may also apply to various other paired devices, such as charging cases, smart watches, smart phones, wrist bands, other wearable devices, hand-held controllers, tablet computers, laptop computers and other external compute devices, etc.

As shown, the neckband 1305 may be coupled to the eyewear device 1302 via one or more connectors. The connectors may be wired or wireless and may include electrical and/or non-electrical (e.g., structural) components. In some cases, the eyewear device 1302 and the neckband 1305 may operate independently without any wired or wireless connection between them. While FIG. 13 illustrates the components of the eyewear device 1302 and the neckband 1305 in example locations on the eyewear device 1302 and the neckband 1305, the components may be located elsewhere and/or distributed differently on the eyewear device 1302 and/or the neckband 1305. In some embodiments, the components of the eyewear device 1302 and the neckband 1305 may be located on one or more additional peripheral devices paired with the eyewear device 1302, the neckband 1305, or some combination thereof.

Pairing external devices, such as the neckband 1305, with augmented-reality eyewear devices may enable the eyewear devices to achieve the form factor of a pair of glasses while still providing sufficient battery and computation power for expanded capabilities. Some or all of the battery power, computational resources, and/or additional features of the augmented-reality system 1300 may be provided by a paired device or shared between a paired device and an eyewear device, thus reducing the weight, heat profile, and form factor of the eyewear device overall while still retaining desired functionality. For example, the neckband 1305 may allow components that would otherwise be included on an eyewear device to be included in the neckband 1305 since users may tolerate a heavier weight load on their shoulders than they would tolerate on their heads. The neckband 1305 may also have a larger surface area over which to diffuse and disperse heat to the ambient environment. Thus, the neckband 1305 may allow for greater battery and computation capacity than might otherwise have been possible on a stand-alone eyewear device. Since weight carried in the neckband 1305 may be less invasive to a user than weight carried in the eyewear device 1302, a user may tolerate wearing a lighter eyewear device and carrying or wearing the paired device for greater lengths of time than a user would tolerate wearing a heavy standalone eyewear device, thereby enabling users to more fully incorporate artificial-reality environments into their day-to-day activities.

The neckband 1305 may be communicatively coupled with the eyewear device 1302 and/or to other devices. These other devices may provide certain functions (e.g., tracking, localizing, depth mapping, processing, storage, etc.) to the augmented-reality system 1300. In the embodiment of FIG. 13, the neckband 1305 may include two acoustic transducers (e.g., 1320(1) and 1320(J)) that are part of the microphone array (or potentially form their own microphone subarray). The neckband 1305 may also include a controller 1325 and a power source 1335.

The acoustic transducers 1320(1) and 1320(J) of the neckband 1305 may be configured to detect sound and convert the detected sound into an electronic format (analog or digital). In the embodiment of FIG. 13, the acoustic transducers 1320(1) and 1320(J) may be positioned on the neckband 1305, thereby increasing the distance between the neckband acoustic transducers 1320(1) and 1320(J) and other acoustic transducers 1320 positioned on the eyewear device 1302. In some cases, increasing the distance between the acoustic transducers 1320 of the microphone array may improve the accuracy of beamforming performed via the microphone array. For example, if a sound is detected by the acoustic transducers 1320(C) and 1320(D) and the distance between the acoustic transducers 1320(C) and 1320(D) is greater than, e.g., the distance between the acoustic transducers 1320(D) and 1320(E), the determined source location of the detected sound may be more accurate than if the sound had been detected by the acoustic transducers 1320(D) and 1320(E).

The controller 1325 of the neckband 1305 may process information generated by the sensors on the neckband 1305 and/or the augmented-reality system 1300. For example, the controller 1325 may process information from the microphone array that describes sounds detected by the microphone array. For each detected sound, the controller 1325 may perform a direction-of-arrival (DOA) estimation to estimate a direction from which the detected sound arrived at the microphone array. As the microphone array detects sounds, the controller 1325 may populate an audio data set with the information. In embodiments in which the augmented-reality system 1300 includes an IMU, the controller 1325 may compute all inertial and spatial calculations from the IMU located on the eyewear device 1302. A connector may convey information between the augmented-reality system 1300 and the neckband 1305 and between the augmented-reality system 1300 and the controller 1325. The information may be in the form of optical data, electrical data, wireless data, or any other transmittable data form. Moving the processing of information generated by the augmented-reality system 1300 to the neckband 1305 may reduce weight and heat in the eyewear device 1302, making it more comfortable to the user.

The power source 1335 in the neckband 1305 may provide power to the eyewear device 1302 and/or to the neckband 1305. The power source 1335 may include, without limitation, lithium ion batteries, lithium-polymer batteries, primary lithium batteries, alkaline batteries, or any other form of power storage. In some cases, the power source 1335 may be a wired power source. Including the power source 1335 on the neckband 1305 instead of on the eyewear device 1302 may help better distribute the weight and heat generated by the power source 1335.

As noted, some artificial-reality systems may, instead of blending an artificial reality with actual reality, substantially replace one or more of a user's sensory perceptions of the real world with a virtual experience. One example of this type of system is a head-worn display system, such as the virtual-reality system 1400 in FIG. 14, that mostly or completely covers a user's field of view. The virtual-reality system 1400 may include a front rigid body 1402 and a band 1404 shaped to fit around a user's head. The virtual-reality system 1400 may also include output audio transducers 1406(A) and 1406(B). Furthermore, while not shown in FIG. 14, the front rigid body 1402 may include one or more electronic elements, including one or more electronic displays, one or more inertial measurement units (IMUS), one or more tracking emitters or detectors, and/or any other suitable device or system for creating an artificial-reality experience.

Artificial-reality systems may include a variety of types of visual feedback mechanisms. For example, display devices in the augmented-reality system 1300 and/or the virtual-reality system 1400 may include one or more liquid crystal displays (LCDs), light-emitting diode (LED) displays, organic LED (OLED) displays, and/or any other suitable type of display screen. Artificial-reality systems may include a single display screen for both eyes or may provide a display screen for each eye, which may allow for additional flexibility for varifocal adjustments or for correcting a user's refractive error. Some artificial-reality systems may also include optical subsystems having one or more lenses (e.g., conventional concave or convex lenses, Fresnel lenses, adjustable liquid lenses, etc.) through which a user may view a display screen.

In addition to or instead of using display screens, some artificial-reality systems may include one or more projection systems. For example, display devices in the augmented-reality system 1300 and/or the virtual-reality system 1400 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial-reality content and the real world. Artificial-reality systems may also be configured with any other suitable type or form of image-projection system.

Artificial-reality systems may also include various types of computer vision components and subsystems. For example, the augmented-reality system 1200, augmented-reality system 1300, and/or virtual-reality system 1400 may include one or more optical sensors, such as 2D or 3D cameras, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions.

Artificial-reality systems may also include one or more input and/or output audio transducers. In the examples shown in FIGS. 12 and 14, the output audio transducers 1208(A), 1208(B), 1406(A), and 1406(B) may include voice coil speakers, ribbon speakers, electrostatic speakers, piezoelectric speakers, bone conduction transducers, cartilage conduction transducers, and/or any other suitable type or form of audio transducer. Similarly, the input audio transducers 1210 may include condenser microphones, dynamic microphones, ribbon microphones, and/or any other type or form of input transducer. In some embodiments, a single transducer may be used for both audio input and audio output.

Figure 14:
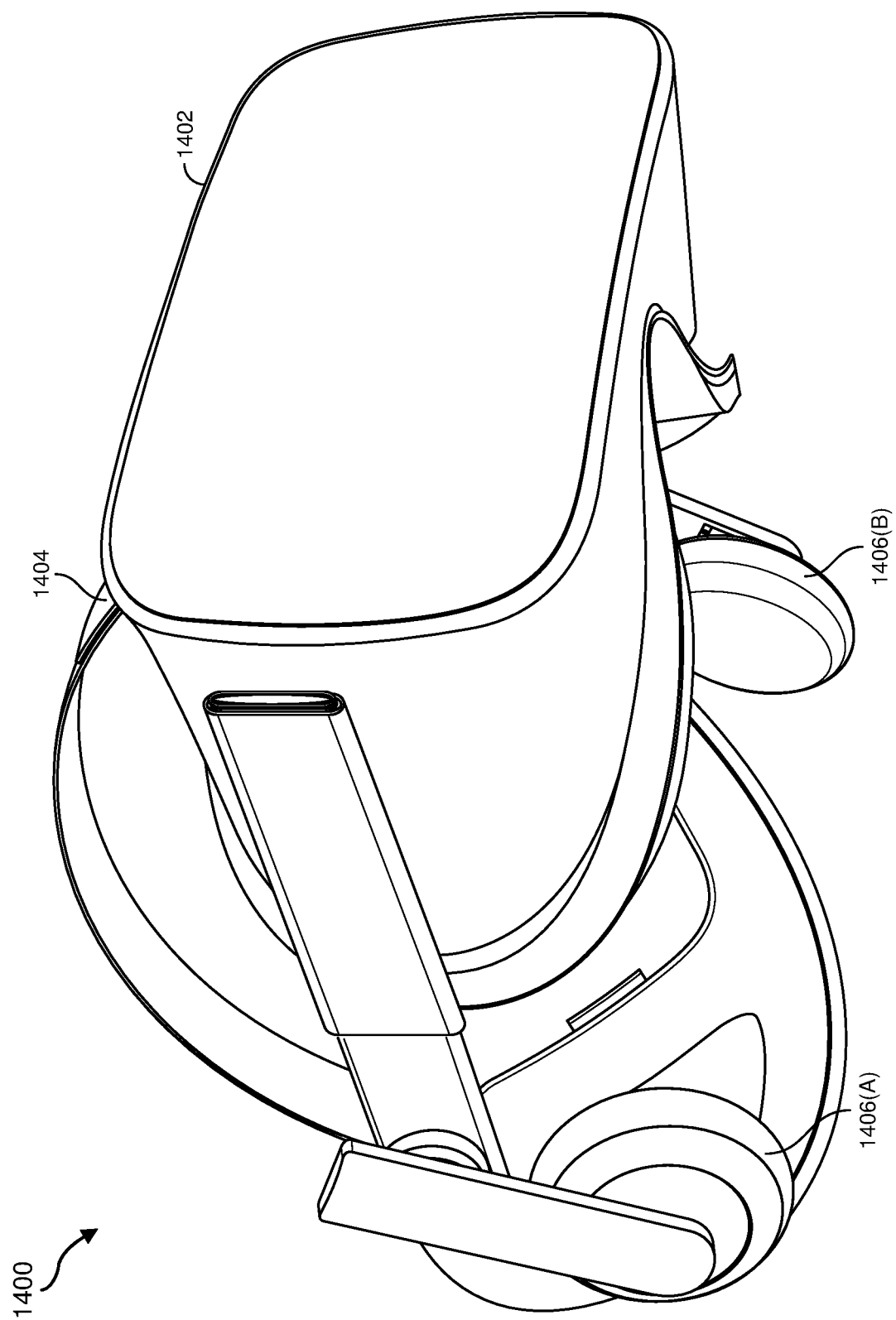
FIG. 14 is an illustration of an example virtual-reality headset that may be used in connection with embodiments of this disclosure.

While not shown in FIGS. 12-14, artificial-reality systems may include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial-reality devices, within other artificial-reality devices, and/or in conjunction with other artificial-reality devices.

By providing haptic sensations, audible content, and/or visual content, artificial-reality systems may create an entire virtual experience or enhance a user's real-world experience in a variety of contexts and environments. For instance, artificial-reality systems may assist or extend a user's perception, memory, or cognition within a particular environment. Some systems may enhance a user's interactions with other people in the real world or may enable more immersive interactions with other people in a virtual world. Artificial-reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visuals aids, etc.). The embodiments disclosed herein may enable or enhance a user's artificial-reality experience in one or more of these contexts and environments and/or in other contexts and environments.

By way of example and not limitation, some embodiments of the present disclosure include the following:

Example 1: An eye-tracking system, including: at least one light source configured to emit, toward a location intended for a user's eye, modulated radiation that is modulated in a manner that enables the light source to be identified by detection and analysis of the modulated radiation; at least one optical sensor including at least one sensing element configured to detect at least a portion of the modulated radiation; and a processor configured to identify, based on the modulated radiation detected by the optical sensor, the light source that emitted the modulated radiation.

Example 2: The eye-tracking system of Example 1, wherein the processor is configured to: determine that the sensing element of the optical sensor has stopped receiving at least a portion of the modulated radiation emitted by the identified light source; and turn off or disregard signals generated by the sensing element of the optical sensor in response to the determination.

Example 3: The eye-tracking system of Example 1 or Example 2, wherein the modulated radiation comprises radiation having a predetermined characteristic, wherein the predetermined characteristic comprises at least one of the following: a predetermined amplitude; a predetermined frequency; or a predetermined phase.

Example 4: The eye-tracking system of any of Examples 1 through 3, further including backend electronics operatively coupled to the optical sensor, wherein the backend electronics are configured to perform at least one operation on a signal from the optical sensor.

Example 5: The eye-tracking system of Example 4, wherein the backend electronics include at least one filter for filtering a signal corresponding to the modulated radiation.

Example 6: The eye-tracking system of Example 5, wherein the filter includes at least one of a passive filter or an active filter.

Example 7: The eye-tracking system of any of Examples 1 through 6, wherein the at least one light source comprises a plurality of light sources and the modulated radiation emitted by each light source of the plurality of light sources is modulated in a manner that enables each light source to be uniquely identified.

Example 8: The eye-tracking system of any of Examples 1 through 7, wherein the at least one optical sensor comprises a plurality of optical sensors, wherein each optical sensor of the plurality of optical sensors is configured to detect a unique waveform of the modulated radiation emitted from the at least one light source.

Example 9: The eye-tracking system of any of Examples 1 through 8, wherein the optical sensor comprises at least one of: a low-resolution optical sensor array including one hundred or fewer sensing elements; or a high-resolution optical sensor array including more than one hundred sensing elements.

Example 10: The eye-tracking system of any of Examples 1 through 9, wherein the processor is configured to perform a fast Fourier transform on a signal from the optical sensor associated with the modulated radiation.

Example 11: The eye-tracking system of any of Examples 1 through 10, further including at least one amplifier electrically coupled to the optical sensor, wherein the amplifier is configured to amplify a signal generated by the optical sensor corresponding to the modulated radiation.

Example 12: The eye-tracking system of Example 11, wherein the amplifier comprises a lock-in amplifier.

Example 13: The eye-tracking system of any of Examples 1 through 12, wherein the light source comprises an infrared light-emitting diode.

Example 14: The eye-tracking system of any of Examples 1 through 13, wherein the sensing element of the optical sensor comprises at least one of: a charge-coupled device sensor; a complementary metal-oxide-semiconductor sensor; a position-sensing detector; or a photodiode sensor.

Example 15: The eye-tracking system of any one of Examples 1 through 14, wherein the sensing element of the optical sensor comprises an event-driven sensing element.

Example 16: A head-mounted display, including: an optical element through which a user views an image, the optical element configured to be worn by the user; at least one light source configured to emit, toward a location intended for the user's eye, modulated radiation that is modulated in a manner that enables the light source to be identified by detection and analysis of the modulated radiation; at least one optical sensor comprising at least one sensing element configured to detect at least a portion of the modulated radiation; and a processor configured to identify, based on the modulated radiation detected by the optical sensor, the light source that emitted the modulated radiation.

Example 17: The head-mounted display of Example 16, further comprising an electronic display associated with the optical element, wherein the electronic display is configured for displaying an image to the user.

Example 18: The head-mounted display of Example 16 or Example 17, wherein the light source is positioned within an optical aperture of the optical element.

Example 19: The head-mounted display of any of Examples 16 through 18, wherein the optical sensor is positioned within an optical aperture of the optical element.

Example 20: A method for eye tracking, including: emitting, by at least one light source, modulated radiation toward a user's eye, the radiation being modulated in a manner that enables the light source to be identified by detection and analysis of the modulated radiation; detecting, by at least one optical sensor comprising at least one sensing element, at least a portion of the modulated radiation reflected off the user's eye; and identifying, by a processor and based on the modulated radiation reflected off the user's eye and detected by the optical sensor, the light source that emitted the modulated radiation to track the user's eye.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

The preceding description has been provided to enable others skilled in the art to best utilize various aspects of the example embodiments disclosed herein. This example description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. An eye-tracking system, comprising:
    at least one light source configured to emit a modulated radiation toward a location intended for a user's eye, the modulated radiation having a different waveform relative to at least one other light source, such that the at least one light source is uniquely identifiable compared to the at least one other light source;
    at least one optical sensor, comprising:
        at least one sensing element configured to detect the waveform of the modulated radiation reflected off the user's eye including detecting whether the waveform has a sinusoidal, a triangular, or a sawtooth shape, and whether an intensity of the modulated radiation reflected off the user's eye reaches a threshold; and
    a processor configured to identify, based on the waveform detected by the at least one optical sensor and whether the waveform has a sinusoidal, a triangular, or a sawtooth shape, and relative to the at least one other light source, the light source that emitted the modulated radiation when the intensity of the modulated radiation reaches the threshold.

2. The eye-tracking system of claim 1, wherein the radiation is modulated according to at least one of amplitude modulation, frequency modulation, pulse-width modulation, waveform modulation, or phase modulation.

3. The eye-tracking system of claim 1, wherein the processor is further configured to:
    determine that the at least one sensing element of the at least one optical sensor has stopped receiving at least a portion of the modulated radiation emitted by the identified light source; and
    turn off or disregard signals generated by the at least one sensing element of the at least one optical sensor in response to the determination.

4. The eye-tracking system of claim 1, further comprising a filter for filtering a signal corresponding to the modulated radiation.

5. The eye-tracking system of claim 1, wherein the at least one light source comprises a plurality of light sources and the modulated radiation emitted by each light source of the plurality of light sources is modulated in a manner that enables each light source to be uniquely identified.

6. The eye-tracking system of claim 1, wherein the at least one optical sensor comprises a plurality of optical sensors, wherein each optical sensor of the plurality of optical sensors is configured to detect a unique waveform of the modulated radiation emitted from the at least one light source.

7. The eye-tracking system of claim 1, wherein the at least one optical sensor comprises a low-resolution optical sensor array including one hundred or fewer sensing elements.

8. The eye-tracking system of claim 7, wherein the at least one optical sensor further comprises a high-resolution optical sensor array including more than one hundred sensing elements.

9. The eye-tracking system of claim 1, wherein the at least one light source comprises an infrared light source.

10. The eye-tracking system of claim 1, wherein the at least one sensing element comprises at least one of:
    a charge-coupled device sensor;
    a complementary metal-oxide-semiconductor sensor;
    a position-sensing detector; or
    a photodiode sensor.

11. The eye-tracking system of claim 1, wherein the eye-tracking system is supported on a head-mounted display.

12. The eye-tracking system of claim 11, wherein the at least one optical sensor is positioned on a frame of the head-mounted display.

13. The eye-tracking system of claim 11, wherein the at least one light source is positioned in an optical aperture of the head-mounted display.

14. The eye-tracking system of claim 11, wherein the head-mounted display comprises augmented-reality glasses.

15. The eye-tracking system of claim 1, wherein the waveform of the modulated radiation comprises a pulsed waveform exhibiting an amplitude and a frequency of pulses.

16. A head-mounted display, comprising:
- an optical element through which a user views an image, the optical element configured to be worn by the user;
- at least one light source configured to emit, toward a location intended for the user's eye, modulated radiation that has a different waveform relative to at least one other light source, that enables the at least one light source to be uniquely identified compared to the at least one other light source by detection and analysis of the modulated radiation;
- at least one optical sensor comprising:
  - at least one sensing element configured to detect at least a portion of the modulated radiation including detecting whether the waveform has a sinusoidal, a triangular, or a sawtooth shape, and whether an intensity of the modulated radiation reaches a threshold; and
- a processor configured to identify, based on the modulated radiation detected by the at least one optical sensor and whether the waveform has a sinusoidal, a triangular, or a sawtooth shape, and relative to the at least one other light source, the light source that emitted the modulated radiation when the intensity of the modulated radiation reaches the threshold.

17. The head-mounted display of claim 16, further comprising an electronic display associated with the optical element, wherein the electronic display is configured for displaying an image to the user.

18. The head-mounted display of claim 16, wherein the light source is positioned within an optical aperture of the optical element.

19. The head-mounted display of claim 16, wherein the optical sensor is positioned within an optical aperture of the optical element.

20. A method for eye tracking, comprising:
- emitting, by at least one light source, modulated radiation toward a user's eye, the modulated radiation having a different waveform relative to at least one other light source to enable the at least one light source to be uniquely identified compared to the at least one other light source by detection and analysis of the modulated radiation;
- detecting, by at least one sensing element of at least one optical sensor, a waveform of the modulated radiation reflected off the user's eye including whether the waveform has a sinusoidal, a triangular, or a sawtooth shape, and whether an intensity of the modulated radiation reflected off the user's eye reaches a threshold; and
- identifying, by a processor and based on the modulated radiation detected by the at least one optical sensor and whether the waveform has a sinusoidal, a triangular, or a sawtooth shape, and relative to the at least one other light source, the light source that emitted the modulated radiation when the intensity of the modulated radiation reaches the threshold.

\* \* \* \* \*